United States Patent
Jeon et al.

(10) Patent No.: US 10,420,815 B2
(45) Date of Patent: Sep. 24, 2019

(54) COMBINATIONAL THERAPY FOR SYNERGISTIC INHIBITION OF GRAM-POSITIVE AND GRAM-NEGATIVE BACTERIA

(71) Applicant: The Governors of the University of Alberta, Edmonton (CA)

(72) Inventors: Byeonghwa Jeon, Edmonton (CA); Jong-Chul Kim, Edmonton (CA)

(73) Assignee: The Governors of the University of Alberta, Edmonton, Alberta (CA)

(*) Notice: Subject to any disclaimer, the term of this patent is extended or adjusted under 35 U.S.C. 154(b) by 0 days.

(21) Appl. No.: 15/760,061

(22) PCT Filed: Sep. 15, 2016

(86) PCT No.: PCT/CA2016/000230
§ 371 (c)(1),
(2) Date: Mar. 14, 2018

(87) PCT Pub. No.: WO2017/045060
PCT Pub. Date: Mar. 23, 2017

(65) Prior Publication Data
US 2018/0256674 A1 Sep. 13, 2018

Related U.S. Application Data

(60) Provisional application No. 62/218,859, filed on Sep. 15, 2015.

(51) Int. Cl.
| | |
|---|---|
| *A61K 31/216* | (2006.01) |
| *A61K 38/12* | (2006.01) |
| *A61K 31/235* | (2006.01) |
| *C07K 7/58* | (2006.01) |
| *A61P 31/04* | (2006.01) |
| *A01N 37/40* | (2006.01) |
| *A01N 43/78* | (2006.01) |
| *A61K 9/00* | (2006.01) |

(52) U.S. Cl.
CPC .............. *A61K 38/12* (2013.01); *A01N 37/40* (2013.01); *A01N 43/78* (2013.01); *A61K 9/0014* (2013.01); *A61K 9/0043* (2013.01); *A61K 31/216* (2013.01); *A61K 31/235* (2013.01); *A61P 31/04* (2018.01); *C07K 7/58* (2013.01); *Y02A 50/473* (2018.01); *Y02A 50/481* (2018.01)

(58) Field of Classification Search
CPC ...... A61K 31/216; A61K 38/12; C07C 69/88; C07K 7/58
See application file for complete search history.

(56) References Cited

U.S. PATENT DOCUMENTS

| 5,358,713 A | 10/1994 | Shimamura |
| 2013/0085103 A1* | 4/2013 | Mohan ................. A61K 9/0014 514/8.2 |
| 2014/0256616 A1* | 9/2014 | Hsu ..................... A61K 31/353 514/2.9 |

FOREIGN PATENT DOCUMENTS

| CA | 2025113 A1 | 8/1991 |
| KR | 100976927 B | 8/2010 |
| WO | 97/47314 | 12/1997 |

OTHER PUBLICATIONS

Soe et al. Action of phytochemicals containing catechins and gallates on Lipoteichoic acid synthesis. International Journal of Integrative Biology. 2012, vol. 13, No. 1, pp. 13-18. (Year: 2012).*
International Search Report for PCT/CA2016/000230, filed Sep. 15, 2016, dated Jan. 20, 2017.
Bellman B. et al. (1998) "Infection with Methicillin-resistant *Staphylococcus aureus* after Carbon Dioxide Resurfacing of the Face," Dermatol. Surg.: 24:279-282.
Daglia M. (2012) "Polyphenols as antimicrobial agents," Current Opinion in Biotechnology, 23:174-181.
Dosler S., & Mataraci E. (2013) "In vitro pharmacokinetics of antimicrobial cationic peptides alone and in combination with antibiotics against methicillin resistant *Staphylococcus aureus* biofilms," Peptides, 49:53-58.
Hatano T. et al. (2005) "Effects of tannins and related polyphenols on methicillin-resistant *Staphylococcus aureus*," Phytochemistry, 66:2047-2055.
John A-K et al. (2009) "Efficacy of Daptomycin in Implant-Associated Infection Due to Methicillin-Resistant *Staphylococcus aureus*: Importance of Combination with Rifampin," Antimicrobial Agents and Chemotherapy, 53 (7):2719-2724.
Kim J-C. & Jeon B. (Jan. 2016) "Novel adjuvant strategy to potentiate bacitracin against MDR MRSA," J Antimicrobial Chemotherapy, 71:1260-1263.
Kondo K. et al. (2006) "ILSMRs (intensifier of beta-lactam-susceptibility in methicillin-resistant *Staphylococcus aureus*) from Tara [Caesalpinia spinosa (Molina) Kuntze]," Phytomedicine, 13:209-212.
Kubo I. et al. (2003) "Non-antibiotic Antibacterial Activity of Dodecyl Gallate," Bioorganic & Medicinal Chemistry, 11:573-580.
Kubo I. et al. (2002) "Anti-MRSA Activity of Alkyl Gallates," Bioorganic & Medicinal Chemistry Letters, 12:113-116.

(Continued)

*Primary Examiner* — Jeffrey E. Russel
(74) *Attorney, Agent, or Firm* — Leydig, Voit & Mayer, Ltd.

(57) ABSTRACT

Compositions and methods for inhibiting the growth of Gram-negative and/or Gram-positive bacteria and pharmaceutical compositions for treating infections of such bacteria in humans and animals are provided. An exemplary method for inhibiting the growth of Gram-negative and/or Gram-positive bacteria includes contacting the bacteria or an environment containing the bacteria with a combination of bacitracin and a gallate ester. An exemplary pharmaceutical composition includes bacitracin and a gallate ester.

20 Claims, 15 Drawing Sheets

(56) References Cited

OTHER PUBLICATIONS

Ming L-J. & Epperson J.D. (2002) "Metal binding and structure—activity relationship of the metalloantibiotic peptide bacitracin," J. Inorganic Biochemistry, 91:46-58.

Pages J-M. & Amaral L. (2009) "Mechanisms of drug efflux and strategies to combat them: Challenging the efflux pump of Gram-negative bacteria," Biochimica et Biophysica Acta, 1794:826-833.

Pandey K.B. & Rizvi S. I. (2009) "Plant polyphenols as dietary antioxidants in human health and disease," Oxidative Medicine and Cellular Longevity, 2(5): 270-278.

Roy R. et al. (2018) posted online Mar. 2017 "Strategies for combating bacterial biofilms: A focus on anti-biofilm agents and their mechanisms of action," Virulence, 9(1): 522-554.

Shibata H. et al. (2009) "Triple Combinations of Lower and Longer Alkyl Gallates and Oxacillin Improve Antibiotic Synergy against Methicillin-Resistant *Staphylococcus aureus*," Antimicrobial Agents Chemotherapy, 53(5): 2218-2220.

Shibata H. et al. (2005) "Alkyl Gallates, Intensifiers of beta-Lactam Susceptibility in Methicillin-Resistant *Staphylococcus aureus*," Antimicrobial Agents Chemotherapy, 49(2): 549-555.

Storm D.R. & Strominger J.L. (1973) "Complex Formation between Bacitracin Peptides and Isoprenyl Pyrophosphates," J. Biological Chemistry, 248 (11):3940-3945.

Suzuki M. et al. (2011) "Antimicrobial Ointments and Methicillin-Resistant *Staphylococcus aureus* USA300," Emerging Infectious Diseases, 17(10):1917-1920.

Wright G.D. (2000) "Resisting resistance: new chemical strategies for battling superbugs," Chemistry & Biology, 7: R127-R132.

\* cited by examiner

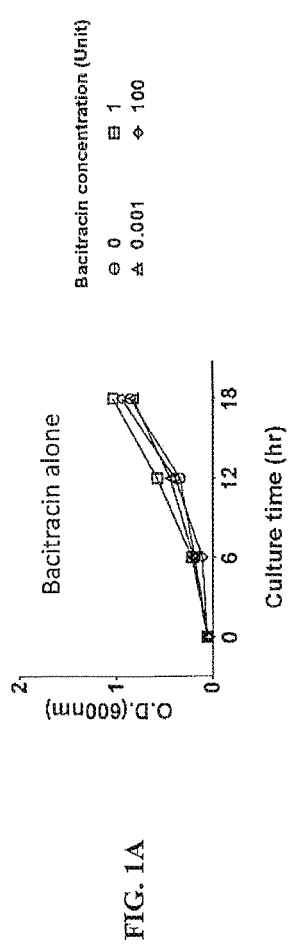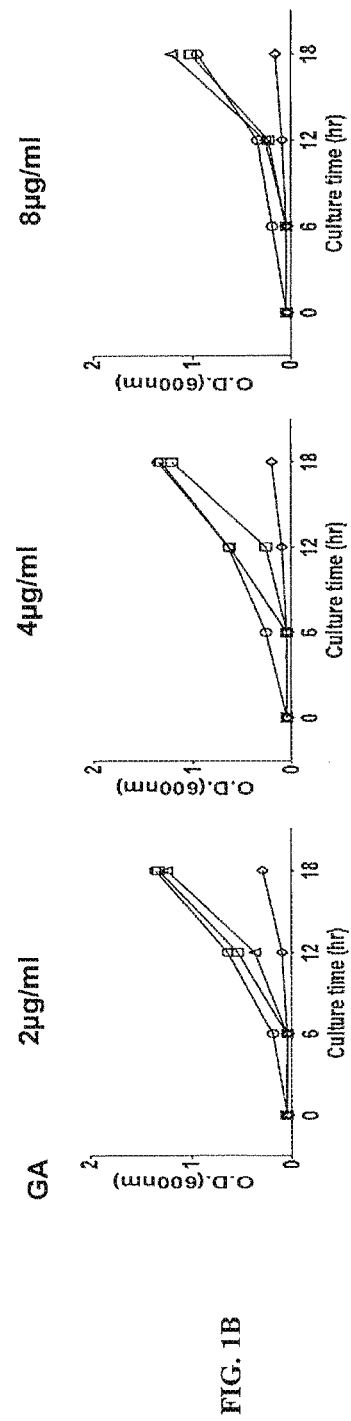
FIG. 1A
FIG. 1B

* The OD increase was caused by the intrinsic color of propyl gallate.

FIG. 8A
(A) BHT:
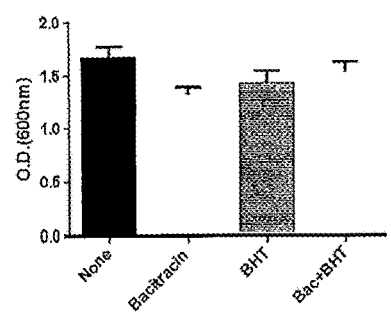
FIG. 8B
(B) Lauryl gallate
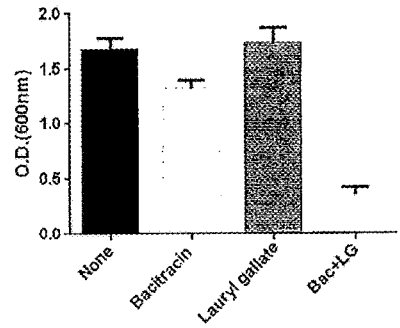
(C) Tannic acid
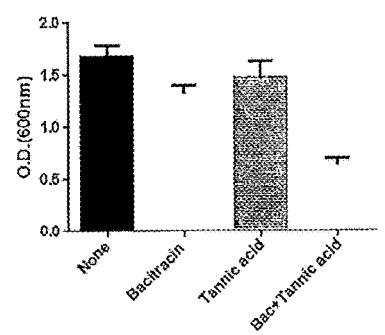
(D) Epigallocatechin gallate (EgCg)
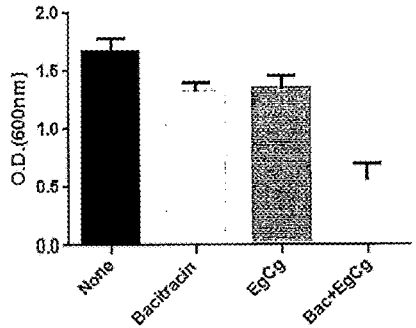
FIG. 8C
FIG. 8D FIG. 9A
FIG. 9B
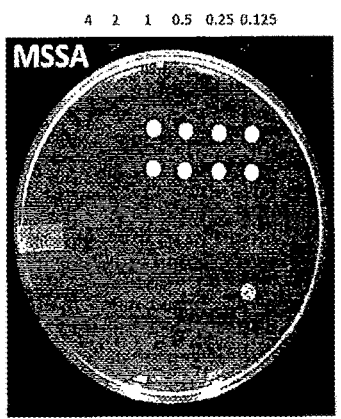
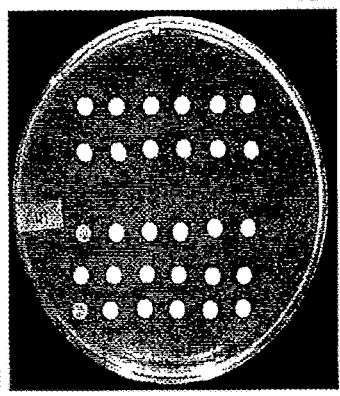
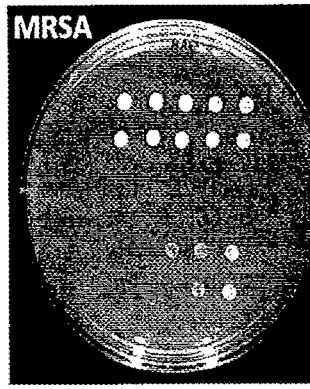
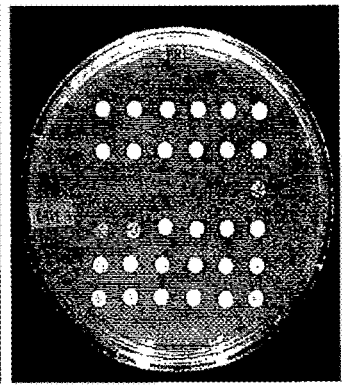
FIG. 9C
FIG. 9D

COMBINATIONAL THERAPY FOR SYNERGISTIC INHIBITION OF GRAM-POSITIVE AND GRAM-NEGATIVE BACTERIA

CROSS-REFERENCE TO RELATED APPLICATIONS

This application is a U.S. National Stage Application under 35 U.S.C. § 371 of International Application No. PCT/CA2016/000230, filed Sep. 15, 2016, which claims the benefit of and priority to U.S. Provisional Application No. 62/218,859, filed Sep. 15, 2015, which is incorporated by reference herein its entirety.

BACKGROUND

Antibiotic resistance is a growing problem encountered with both Gram-positive and Gram-negative bacteria. Particularly, multi-drug resistant (MDR) bacteria exhibit at least in vitro resistance to more than one antibacterial agent. Infections by such MDR bacteria are generally more difficult to treat and result in poorer patient outcomes. Exemplary clinically significant Gram-positive bacteria include *Staphylococcus, Streptococcus, Corynebacterium, Listeria, Bacillus* and *Clostridium*. Exemplary clinically significant Gram-negative bacteria include certain *Escherichia coli* strains, *Salmonella, Shigella, Enterobacter, Pseudomonas, Neisseria, Klebsiella*, and *Acinetobacter*.

*Staphylococcus aureus* causes a wide range of infections in animals and humans[1], including skin and soft tissue infections, both minor (e.g., boils) and major (e.g., furunculosis) infections[2], and even fatal infections such as endocarditis, necrotizing fasciitis, and toxic shock syndrome[3]. In addition, *S. aureus* easily develops antibiotic resistance and antibiotic-resistant *S. aureus*, particularly methicillin-resistant *S. aureus* (MRSA), seriously threatens public health. MRSA infections usually occur in hospital environments where antibiotics are heavily used[4,5]. Although several new anti-MRS A agents have been introduced, MRSA still remains resistant to various drugs of clinical importance and difficult to treat[6]. In addition, the combination of multidrug resistance with hyper-virulence in MRSA may cause infections in patients as well as healthy people outside the hospital setting[7]. Since about 30% of the population commonly carries *S. aureus*, a significant number of people are discharged from hospital as asymptomatic carriers and disseminate MRSA to the community[8]. Recently, community-associated methicillin-resistant *S. aureus* (CA-MRSA) has become much more notorious in the community[9-12], causing suppurative skin infections (e.g., epidemics of furunculosis) and even life-threatening clinical problems, such as necrotizing fasciitis, and necrotizing pneumonia[13]. In addition, new strains of CA-MRSA that are highly transmissible and more resistant spread rapidly in communities[8]. For example, MRSA USA300 emerged and now accounts for 97-99% of MRSA isolated from skin and soft-tissue infections in the US[14,15], and a similar pattern of MRSA infections is also observed in Canada[16,17].

Over-the-counter antimicrobial ointments containing bacitracin, polymyxin, neomycin, and/or gramicidin are commonly used to treat skin injuries and infections[18,19] Over-the-counter ointments, such as Polysporin® antibiotic ointment, commonly contain antimicrobial peptides (i.e., polymyxin B and bacitracin) as medical ingredients, and non-medical ingredients, such as olive oil, cotton seed oil, cocoa butter, peptrolatum, sodium pyruvate, vitamin E, and butylated hydroxytoluene (BHT). Among the medical ingredients, bacitracin is the antimicrobial agent that may inhibit Gram-positive pathogens, such as *S. aureus*. Other non-medicinal ingredients are mostly oily materials, as ointment bases, and antioxidants (such as BHT, vitamin E, and sodium pyruvate) to prevent lipid oxidation in the ointment. However, a previous study reported that USA300 is resistant to bacitracin and neomycin, the major antimicrobial agents in ointments, suggesting that existing ointments cannot kill USA300 and rather selectively enrich the population of this hyper-resistant MRSA strain[19]. Since biofilm formation is a critical step for bacterial infection, the inhibition of biofilm formation is important for the treatment. Bacterial cells in biofilms are more resistant to antibiotics than free-living planktonic cells. MRSA also frequently forms biofilms during infection; this makes the treatment even more difficult.

While most *E. coli* do not cause disease, certain virulent strains are associated with gastroenteritis, urinary tract infections, and neonatal meningitis, and more rarely with hemolytic-uremic syndrome, peritonitis, mastitis, septicaemia and gram-negative pneumonia. Enterohemorrhagic *E. coli* strains, such as O157:H7, produce a deadly toxin called Shiga-like toxin associated with food poisoning. *E. coli* strains are also responsible for a significant portion of infections associated with hospitalization[36]. There are reports of increasing antibiotic resistance and multi-drug resistance in pathogenic *E. coli* strains, such as Extended Spectrum β-Lactamase (ESBL)-producing *E. coli*[37,38]

*Salmonella* is a genus of the Enterobacteriaceae family, strains of which are associated with food poisoning (*salmonellosis*) as well as typhoid and paratyphoid fever. Of most interest as human pathogens are *Salmonella enterica*, which are divided into six subspecies and over 2500 serovars. For example, *Salmonella enterica* servovar. *Typhimurium* (*S. Typhimurium*) is a significant agent of food poisoning. *Salmonella enterica* servovar. *Typhi* (*S. Typhi*) is associated with typhoid fever. There are reports of increasing antibiotic resistance and multi-drug resistance in *Salmonella enterica*.[39,40]

Due to increasing drug resistance in both Gram-negative and Gram-positive bacteria, there is a great need for developing effective antimicrobial compounds that have new modes of action. Alternatively, the development of antimicrobial adjuvants that inhibit the function of resistance determinants is considered as a novel approach to curb antibiotic resistance[20], because this alternative strategy may re-sensitize pathogens to antibiotics and enhance the utility of existing antibiotics[20,21].

Previously, certain phenolic compounds present in plant extracts were reported to exhibit antimicrobial activity[22]. There are various reports of antibiotic and antimicrobial activity of phenols and polyphenols[31-35]. In addition, some studies report that certain phenolic compounds intensify the antimicrobial activity of β-lactams[23-25]. Many kinds of phenolic compounds have been approved by the U.S. FDA as antioxidants for ointments, cosmetics, and even for food additives[26]. For example, BHT is used as an antioxidant in Polysporin® antibiotic ointment. The present disclosure relates to phenolic antioxidants, particularly gallic acid esters, which exhibit synergistic antimicrobial activity with bacitracin to inhibit Gram-positive bacteria including hyper-resistant MRSA strains. The combinations also exhibited significant antimicrobial effects against some Gram-negative pathogens that are intrinsically resistant to bacitracin. In addition, the combination exhibited a significant anti-biofilm activity against MRSA USA300.

SUMMARY

This disclosure relates to compositions and methods for inhibiting the growth of Gram-negative and/or Gram-positive bacteria and pharmaceutical compositions for treating infections of such bacteria in humans and animals.

The disclosure provides a method for inhibiting the growth of Gram-negative and/or Gram-positive bacteria which comprises contacting the bacteria or an environment containing the bacteria with a combination of bacitracin and at least one gallate ester. In embodiments, the gallate ester is an alkyl gallate ester. Alkyl groups include those having 1 to 20 carbons. In embodiments, the gallate ester is octyl gallate. In embodiments the gallate ester is lauryl gallate. In other embodiments, the gallate ester is an aryl gallate ester. In embodiments, aryl groups include unsubstituted phenyl and phenyl substituted with one or more hydroxyl group. In specific embodiments, the aryl group is a 3, 4, 5-trihydroxyphenyl group. In specific embodiments, only one gallate ester is present in the combination. In specific embodiments, the only active antibacterial agents in the combination are bacitracin and the one or more gallate esters. In specific embodiments, the only active antibacterial agents in the combination are bacitracin and one gallate ester.

In embodiments, the bacteria inhibited are Gram-positive bacteria. In embodiments, the bacteria are *Staphylococcus aureus*. In embodiments, the bacteria are methicillin-resistant *Staphylococcus aureus*. In embodiments, the bacteria are methicillin-sensitive *Staphylococcus aureus*. In embodiments, the bacteria are "multidrug resistant" *Staphylococcus aureus*.

In embodiments, the bacteria are Gram-negative bacteria. In embodiments, the bacteria are bacitracin-resistant Gram-negative bacteria. In embodiments the bacteria are pathogenic *E. coli*. In embodiments, the bacteria are *Salmonella* strains. In embodiments, the bacteria are *Salmonella enterica* strains.

The combination of bacitracin and gallate ester is synergistic, such that contact of the combination with the bacteria or an environment of the bacteria exhibits a higher than additive effect compared to contact with the components (bacitracin and gallate ester) individually. In a specific embodiment, the weight ratio of bacitracin to gallate ester is less than or equal to 0.1. In a specific embodiment, the weight ratio of bacitracin to gallate ester is less than or equal to 0.02. In these embodiments, both bacitracin and gallate ester are present in the combination.

The disclosure provides a method for treating a bacterial infection in an individual in need of such treatment which comprises administering to the individual a combined effective amount of bacitracin and at least one gallate ester. In an embodiment, the gallate ester is an alkyl gallate ester, wherein the alkyl group has 1 to 20 carbon atoms. In an embodiment, the gallate ester is octyl gallate. In an embodiment, the gallate ester is lauryl gallate. In embodiments, the gallate ester is an aryl gallate ester. In embodiments, aryl groups include unsubstituted phenyl and phenyl substituted with one or more hydroxyl group. In specific embodiments, the aryl group is a 3, 4, 5-trihydroxyphenyl group. In specific embodiments, only one gallate ester is present in the combination. In specific embodiments, the only active antibacterial agents in the combination are bacitracin and the one or more gallate esters. In specific embodiments, the only active antibacterial agents in the combination are bacitracin and one gallate ester.

In embodiments, the bacteria inhibited are Gram-positive bacteria. In embodiments, the bacteria are *Staphylococcus aureus*. In embodiments, the bacteria are methicillin-resistant *Staphylococcus aureus*. In embodiments, the bacteria are methicillin-sensitive *Staphylococcus aureus*. In embodiments, the bacteria are "multidrug resistant" *Staphylococcus aureus*.

In embodiments, the bacteria are Gram-negative bacteria. In embodiments, the bacteria are bacitracin-resistant Gram-negative bacteria. In embodiments the bacteria are pathogenic *E. coli*. In embodiments, the bacteria are *Salmonella* strains. In embodiments, the bacteria are *Salmonella enterica* strains.

The combination can be administered by any conventional method. In an embodiment, the combination of bacitracin and gallate ester are administered topically.

In a specific embodiment, the disclosure provides a method for treatment of wounds to prevent or inhibit infection thereof which comprises applying to the wound a combination of bacitracin and a gallate ester. More specifically the combination is a synergistic combination.

The disclosure provides a combination of bacitracin and at least one gallate ester wherein bacitracin and the at least one gallate ester are present in the combination in an amount or in relative amounts such that the combination exhibits a synergistic effect on inhibition of a Gram-positive or Gram-negative bacteria. In a specific embodiment, the specific embodiment, the weight ratio of bacitracin and gallate ester are present in the combination. 0.02. In these embodiments, both bacitracin and gallate ester are present in the combination.

The disclosure provides pharmaceutical compositions which comprise bacitracin and at least one gaUate ester. In a specific embodiment, the weight ratio of bacitracin to the at least one gallate ester is less than or equal to 0.1. In a specific embodiment, the weight ratio of bacitracin to gallate ester is less than or equal to 0.02. In these embodiments, both bacitracin and gallate ester are present in the combination. In specific embodiments of the pharmaceutical composition, the gallate ester is octyl gallate or lauryl gallate.

The disclosure further provides a composition and method for inhibition of biofilm formation or disruption of biofilms which comprises contacting the environment of the biofilm with a combination of bacitracin and at least one gallate ester. In a specific embodiment, the weight ratio of bacitracin to the at least one gallate ester is less than or equal to 0.1. In a specific embodiment, the weight ratio of bacitracin to gallate ester is less than or equal to 0.02. In these embodiments, both bacitracin and gallate ester are present in the combination. In specific embodiments, the gallate ester is octyl gallate or lauryl gallate.

BRIEF DESCRIPTION OF THE FIGURES

FIGS. 8A, 8B, 8C, 8D. Inhibition of MRSA with bacitracin and some phenolic compounds, including BHT (A), lauryl gallate (B), tannic acid (C), and EgCg (D). Whereas BHT, the phenolic antioxidant used in Polysporin, did not show any synergistic antimicrobial effects with bacitracin, the other three antioxidants significantly inhibited MRSA. The concentrations of bacitracin and phenolic antioxidants were 0.002 µg/ml (ca., 0.0002 U) and 0.5 µg/ml, respectively.

FIGS. 9A, 9B, 9C, 9D. Synergistic killing of methicillin-sensitive *S. aureus* (MSSA) and MRSA with bacitracin and phenolic antioxidants. The white spots indicate bacterial growth and show the bactericidal levels. The strains were aerobically cultured 18 h in MH liquid media with different concentrations of bacitracin and 0.5 µg/ml of each phenolic compound, and 10 µl of the culture was spotted on MH agar plates and incubated at 37° C. overnight.

DETAILED DESCRIPTION

Figure 1C:
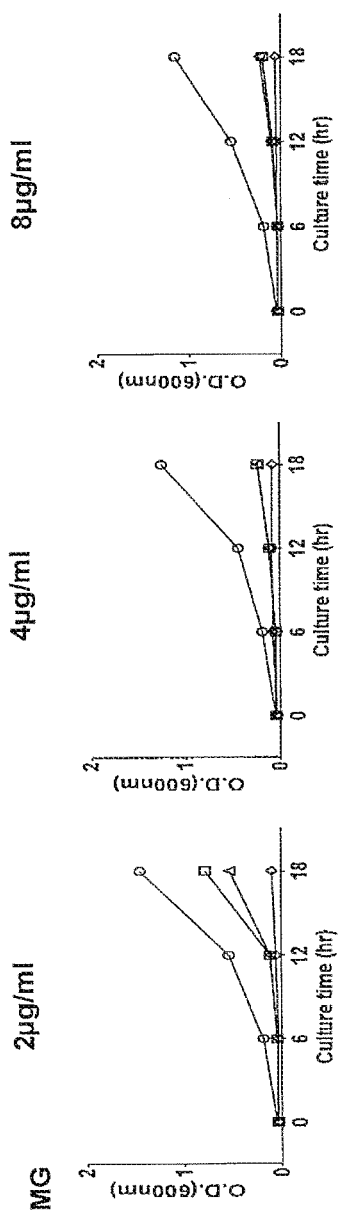
FIGS. 1A, 1B, 1C, 1D, 1E, IF, 1G, 1H, 1I. Growth inhibition of USA300 by bacitracin and alkyl gallates. The results are representative of three independent experiments that showed similar growth patterns. GA: gallic acid, MG: methyl gallate, EG: ethyl gallate, PG: propyl gallate, BG: butyl gallate, OG: octyl gallate, LG: lauryl gallate, SG: stearyl gallate.
Figure 1D:
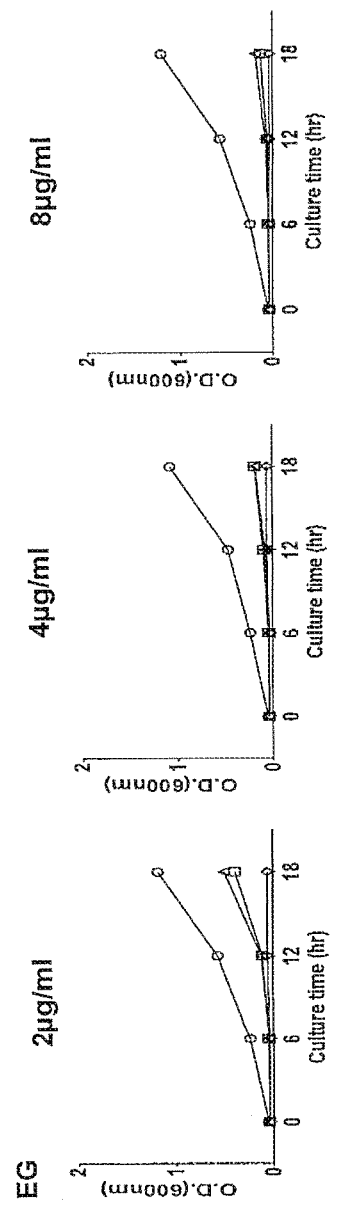
Figure 1E:
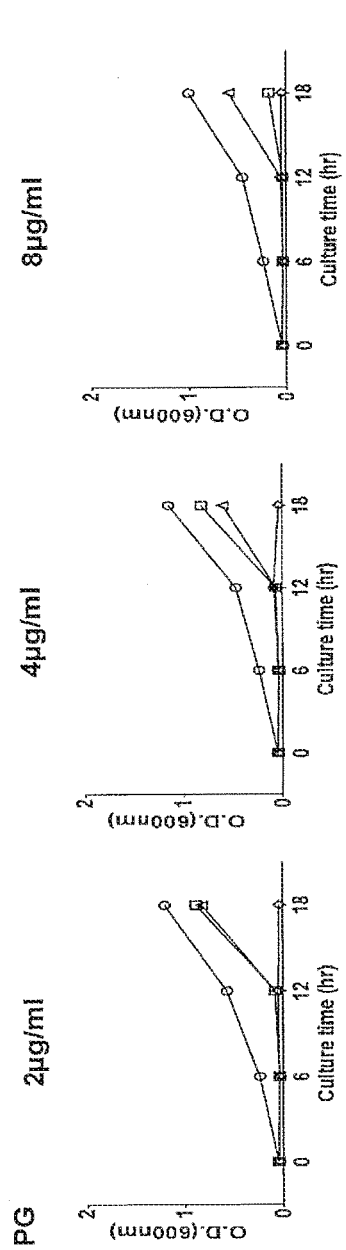
Figure 1F:
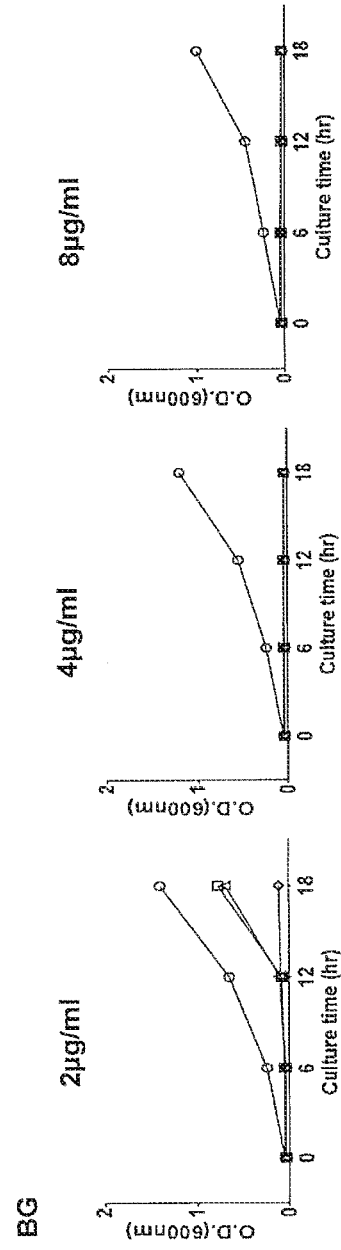

This disclosure relates to a synergistic combination of bacitracin and one or more gallate esters for inhibition of Gram-negative and/or Gram-positive bacteria. The combinations of this disclosure are of specific application to inhibition of Gram-positive *Staphylococcus* strains and more particularly *Staphylococcus aureus* strains and Gram-negative pathogenic *Escherichia coli* strains and *Salmonella* strains.

Gallate esters useful in the invention include those of formula:

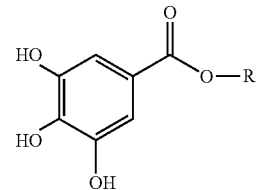

and salts thereof (if any),
where R is an alkyl group, an arylalkyl group, an aryl group or a optionally substituted chromanyl group, wherein the aryl groups are optionally substituted with one or more hydroxyl groups, carboxylate groups or carboxylate ester groups and wherein the chromanyl group is optionally substituted with one or more hydroxyl groups, carboxylate, carboxylate ester or aryl groups.

In specific embodiments, alkyl groups are straight chain or branched alkyl groups. In specific embodiments, alkyl groups are branched alkyl groups having 4-6 carbon atoms, including all isomers thereof.

In specific embodiments, R is an unsubstituted alkyl group having 1 to 20 carbon atoms. In more specific embodiments, R is an unsubstituted alkyl group having 1 to 6 carbon atoms. In more specific embodiments, R is an unsubstituted alkyl group having 6 to 12 carbon atoms. In more specific embodiments, R is an unsubstituted alkyl group having 10-18 carbon atoms. In more specific embodiments, R is an unsubstituted alkyl group having 8-18 carbon atoms. In more specific embodiments, R is an unsubstituted alkyl group having 8-16 carbon atoms. In more specific embodiments, R is an unsubstituted alkyl group having 10-16 carbon atoms. In more specific embodiments, R is an unsubstituted alkyl group having 12-16 carbon atoms. In more specific embodiments, R is octyl group. In more specific embodiments, R is a lauryl group. In more specific embodiments, R is a stearyl group.

In specific embodiments, R is a chromanyl group. In specific embodiments, R is a chroman-3-yl group:

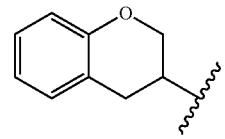 [SMILES: *C1COc2ccccc2C1]

In specific embodiments, R is a 5,7-dihydroxychroman-3-yl group:

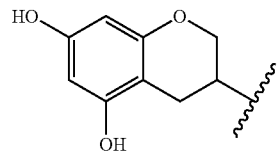 [SMILES: *C1COc2cc(O)cc(O)c2C1]

In specific embodiments, R is an optionally substituted chromanyl group, wherein the optional substitution is substitution with one or more one or more hydroxyl groups, one or more optionally substituted aryl groups, carboxylate groups or carboxylate ester groups. In specific embodiments, R is a hydroxyl-substituted chromanyl group. In specific embodiments, R is a phenyl substituted chromanyl group. In specific embodiments, the chromanyl group is substituted at the 2 position with a phenyl group, a monohydroxy substituted phenyl group, a dihydroxy substituted phenyl group or a trihydroxy substituted phenyl group.

In specific embodiments, R is

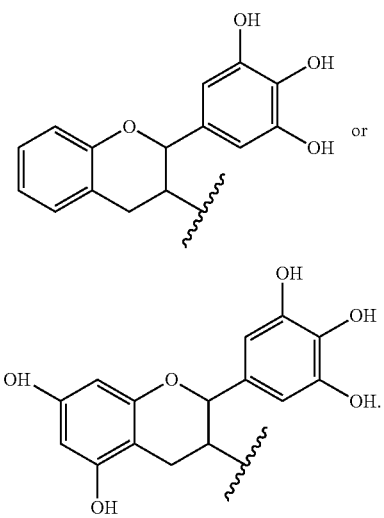 [SMILES: *C1Cc2ccccc2OC1c1cc(O)c(O)c(O)c1 ; *C1Cc2c(O)cc(O)cc2OC1c1cc(O)c(O)c(O)c1]

In specific embodiments, R is

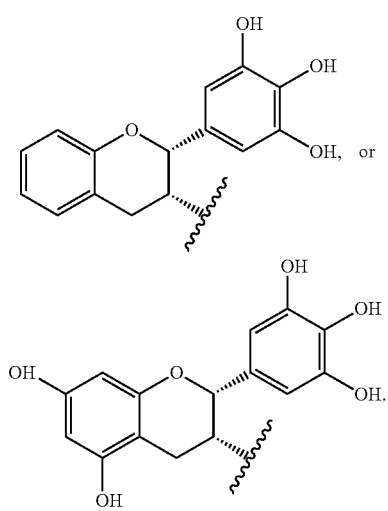 [SMILES: *[C@@H]1Cc2ccccc2O[C@@H]1c1cc(O)c(O)c(O)c1 ; *[C@@H]1Cc2c(O)cc(O)cc2O[C@@H]1c1cc(O)c(O)c(O)c1]

In specific embodiments, R is a phenyl group. In specific embodiments, R is an alkyl group substituted with an aryl group (arylalkyl group), wherein the alkyl group has 1 to 3 carbons. In specific embodiments, the aryl group of the aryl alkyl group is a phenyl group. In specific embodiments, the arylalkyl group is a benzyl group or a phenethyl group. In specific embodiments, the aryl group of the arylalkyl group is a phenyl group or a phenyl group substituted with one or more hydroxyl groups, a carboxylate or a carboxylate ester group. In specific embodiments, the aryl group is a 2, 3, 4-trihydroxyphenyl group. In specific embodiments, the aryl group of the arylalkyl group is a 2, 3, 4-trihydroxyphenyl group.

In specific embodiments, the gallate ester is digallic acid or an alkyl or aryl ester thereof:

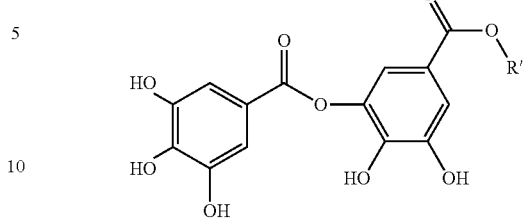

and salts thereof (if any):

where R' is hydrogen, an alkyl group, an arylalkyl group or an aryl group, wherein the aryl groups are optionally substituted with one or more hydroxyl groups, carboxylate groups or carboxylate ester groups. In specific embodiments, R' is hydrogen (digallic acid). In specific embodiments, R' is an alkyl group having 1-20 carbon atoms. In specific embodiments, R' is an alkyl group having 1-6 carbon atoms. In specific embodiments, R' is an alkyl group having 8-18 carbon atoms. In specific embodiments, R' is an alkyl group having 8-16 carbon atoms. In more specific embodiments, R' is octyl group. In more specific embodiments, R' is a lauryl group. In more specific embodiments, R' is a stearyl group. In specific embodiments, R' is a phenyl, benzyl or phenethyl group. In specific embodiments, R' that is an aryl or an arylalkyl group is substituted with one or more hydroxyl groups, carboxylate groups or carboxylate ester groups.

In specific embodiments, the gallate ester is digallic acid or an alkyl or aryl ester thereof:

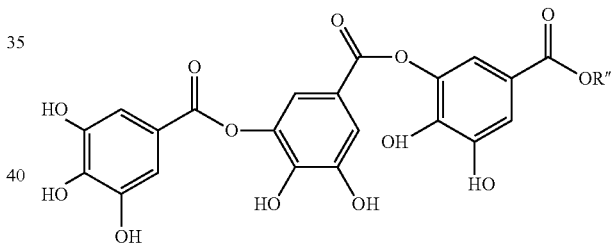

and salts thereof (if any):

where R" is hydrogen, an alkyl group, an arylalkyl group or an aryl group, wherein the aryl groups are optionally substituted with one or more hydroxyl groups, carboxylate groups or carboxylate ester groups. In specific embodiments, R" is hydrogen (trigallic acid). In specific embodiments, R" is an alkyl group having 1-20 carbon atoms. In specific embodiments, R" is an alkyl group having 1-6 carbon atoms. In specific embodiments, R" is an alkyl group having 8-18 carbon atoms. In specific embodiments, R" is an alkyl group having 8-16 carbon atoms. In more specific embodiments, R" is octyl group. In more specific embodiments, R" is a lauryl group. In more specific embodiments, R" is a stearyl group. In specific embodiments, R" is a phenyl, benzyl or phenethyl group. In specific embodiments, R" that is an aryl or an arylalkyl group is substituted with one or more hydroxyl groups, carboxylate groups or carboxylate ester groups.

In specific embodiments, the gallate ester is tannic acid.

The terms alkyl or alkyl group refer to a monoradical of a straight-chain or branched saturated hydrocarbon and to cycloalkyl groups having one or more rings. Alkyl groups include straight-chain, and branched alkyl groups. Alkyl groups may include portions that are straight-chain, or branched. Unless otherwise indicated alkyl groups have 1-20 carbon atoms (C1-C20 alkyl groups). In specific embodiments, alkyl groups contain 1 to 3 carbon atoms (C1-C3 alkyl groups). Alkyl groups also include larger alkyl groups having 8 or more carbon atoms. Exemplary alkyl groups include methyl, ethyl, n-propyl, iso-propyl, n-butyl, s-buty, t-butyl, n-pentyl, iso-pentyl, s-pentyl, n-hexyl, branched hexyl, n-heptyl, n-octyl, n-nonyl, n-decyl, n-dodecyl (lauryl), n-stearyl (C16), all of which are optionally substituted.

Aryl groups include groups having one or more 5- or 6-member aromatic rings. Aryl groups can contain one, two or three, 6-member aromatic rings. Aryl groups can contain two or more fused aromatic rings. Aryl groups can contain two or three fused aromatic rings. Aryl groups are optionally substituted with one or more non-hydrogen substituents. Substituted aryl groups include among others those which are substituted with alkyl or alkenyl groups, which groups in turn can be optionally substituted. Preferred substitution is with one or more hydroxyl groups, carboxylate groups or carboxylate ester groups. Specific aryl groups include phenyl groups, biphenyl groups, pyridinyl groups, and naphthyl groups, all of which are optionally substituted as described herein. Substituted aryl groups those having 1, 2 or 3 hydroxyl groups, those having a single carboxylate group or a single carboxylate ester group or combinations of 1, 2, or 3 hydroxyl and one carboxylate or one carboxylate ester.

Arylalkyl groups are alkyl groups substituted with an aryl groups, where alkyl and aryl groups are defined above. Specific alkyl groups of aryl alkyl groups are methyl, ethyl and propyl groups. Specific aryl groups of arylalkyl groups are phenyl groups and substituted phenyl groups.

Carboxylate ester groups (—COOR$^1$) which are substituents include those in which the ester (R$^1$) is an alkyl, aryl or arylalkyl group. Specific R$^1$ include alkyls having 1-3 carbon atoms, alkyl groups having 3-6 carbon atoms, alkyl groups having 8-16 carbon atoms, alkyl groups having 8 carbons, or alkyl groups having 12 carbons. Specific R$^1$ can also be phenyl or hydroxy-substituted phenyl.

Compositions of this invention include bacitracin. Bacitracin is a polypeptide antibiotic which is a mixture of cyclic peptides produced during growth of Bacillus subtilis, the main components of the mixture are Bacitracin A, B1, and B2. Bacitracin for clinical use is prepared in an ointment for topical application or in the form of a powder or lyophilized powder for preparation of injectables. Bacitracin is also employed as bacitracin zinc salt. The term bacitracin as used herein includes any form of bacitracin presently in clinical use. All such forms of bacitracin can be employed in the compositions and methods herein. Bacitracin typically has a minimum potency ranging from 40-60 IU/mg.

Bacitracin is often used in combination with other antibiotics, particularly polymixin and neomycin. Antibacterial compositions herein optionally include polymixin and neomycin or other antibiotics that are presently employed clinically in combination with bacitracin.

This disclosure provides pharmaceutical compositions comprising a synergistic combination of bacitracin and one or more gallate esters. Pharmaceutical compositions include among others ointments, salves, creams, gels, hydrogels, lotions, pastes sprays or foams for topical administration. Various pharmaceutical compositions forms for injection are also included. Administration by injection includes subcutaneous injection, intravenous injection, intramuscular injections, intraperitoneal injection or instillation. Injectable preparations, for example, sterile injectable aqueous suspensions or oil suspensions can be prepared by known methods. Pharmaceutical compositions also include those suitable for ophthalmic application, e.g., eye drops.

Pharmaceutical compositions herein can be formulated for topical administration, for example, with a suitable ointment containing the combination of bacitracin and at least one gallate ester or any salts thereof suspended or dissolved in a carrier, which include mineral oil, liquid petroleum, white petroleum, propylene glycol, polyoxyethylene polyoxypropylene compound, emulsifying wax and pharmaceutically acceptable water. In addition, topical formulations can be formulated with a lotion or cream containing the antibacterially active compounds suspended or dissolved in a carrier. Suitable carriers include mineral oil, sorbitan monostearate, polysorbate 60, cetyl esters wax, cetearyl alcohol, 2-octyldodecanol, benzyl alcohol and pharmaceutically acceptable water.

Pharmaceutical compositions contain a combined therapeutically effective amount of bacitracin and one or more gallate esters. The combined therapeutically effective amount refers to the amount of bacitracin and gallate ester as antibacterial active ingredients that inhibit or prevent bacterial growth or which exhibit a measurable therapeutic or prophylactic effect. The effective amount that is used for any given patient in any given dosage form will depend upon the dosage form, severity of disease or infection and patient (weight, health status, etc.). One of ordinary skill in the art, employing known methodologies understands how to establish amounts of active components needed to be effective for control or prevention of bacterial infection.

The term synergistic (or synergy) refers to a non-additive effect of a combination or two or more ingredients. More specifically, the non-additive effect is assessed by any method for assessing inhibition of growth or assessing killing of bacteria. Assessment of inhibition or cell death may be in vitro (for example as in examples herein) or in vivo (on treatment of an individual). One or both of the components may exhibit little or no effect when administered to the bacteria. On combination of the components, a non-additive effect is observed. Synergistic combination refers to the relative amounts of components that result in a synergistic effect. In the present disclosure this refers to the relative amounts of bacitracin and the one or more gallate esters combined. It will be understood that synergistic concentrations will depend on the specific forms of bacitracin and the specific gallate ester or combination of esters employed.

In the present disclosure, synergistic compositions include those in which the amount of gallate ester ranges generally from 0.3 ug to 30 μg of gallate ester to 100 IU of bacitracin. More specifically, the amount of gallate ester ranges from 0.1 μg to 10 μg to 100 IU of bacitracin. More specifically, the amount of gallate ester ranges from 0.5 μg to 5 μg to 100 IU of bacitracin. More specifically, the amount of gallate ester ranges from 1.0 μg to 5 μg to 100 IU of bacitracin.

In an exemplary ointment composition containing 500 IU of bacitracin/gram of ointment, the amount of gallate ester in the composition ranges from 1.5 μg to 150 μg of gallate ester. More specifically, the amount of gallate ester in a 500 IU of bacitracin/gram composition ranges from 3 μg to 30 μg of gallate ester. More specifically, the amount of gallate ester in a 500 IU of bacitracin/gram composition, ranges from 5 μg to 25 μg of gallate ester. More specifically, the amount of gallate ester in a 500 IU of bacitracin/gram composition ranges from 10 μg to 20 μg of gallate ester.

In specific embodiments, the weight ratio of bacitracin to gallate ester is less than 0.1. In specific embodiments, the weight ratio of bacitracin to gallate ester is less than 0.02. In specific embodiments, the weight ratio of bacitracin to gallate ester is less than 0.01. In specific embodiments, the weight ratio of bacitracin to gallate ester is less than 0.001. In specific embodiments, the weight ratio of bacitracin to gallate ester is less than 0.0001.

In specific embodiments, the weight ratio of bacitracin to lauryl gallate is less than 0.1. In specific embodiments, the weight ratio of bacitracin to lauryl gallate is less than 0.02. In specific embodiments, the weight ratio of bacitracin to octyl gallate is less than 0.1. In specific embodiments, the weight ratio of bacitracin to octyl gallate is less than 0.02. In specific embodiments, the weight ratio of bacitracin to lauryl gallate ranges from 0.02-0.00005. In specific embodiments, the weight ratio of bacitracin to lauryl gallate is less than 0.004. In specific embodiments, the weight ratio of bacitracin to lauryl gallate is less than 0.008. In specific embodiments, the weight ratio of bacitracin to octyl gallate ranges from 0.0002 to 0.000005. In specific embodiments, the weight ratio of bacitracin to octyl gallate ranges from 0.0002-0.0000025.

Useful combinations of the at least one gallate ester with bacitracin results in decrease in in the MIC of the combination compared to that of the bacitracin alone of at least 2-fold. In embodiments, the MIC of the combination is decreased by at least 100-fold compared to the bacitracin alone. In embodiments, the MIC of the combination is decreased by at least 500-fold compared to the bacitracin alone. In embodiments, the MIC of the combination is decreased by at least 1000-fold compared to the bacitracin alone. In embodiments, the MIC of the combination is decreased by at least 2000-fold compared to the bacitracin alone. In embodiments, the MIC of the combination is decreased by at least 5000-fold compared to the bacitracin alone. In embodiments, the MIC of the combination is decreased by at least 10,000-fold compared to the bacitracin alone. In embodiments, the MIC of the combination is decreased by at least 100,000-fold compared to the bacitracin alone. In embodiments, the MIC of the combination is decreased by at least 200,000-fold compared to the bacitracin alone.

Useful combinations of the at least one gallate ester with bacitracin results in decrease in the MBC of the combination compared to that of the bacitracin alone of at least 2-fold. In embodiments, the MBC of the combination is decreased by at least 100-fold compared to the bacitracin alone. In embodiments, the MBC of the combination is decreased by at least 500-fold compared to the bacitracin alone. In embodiments, the MBC of the combination is decreased by at least 1000-fold compared to the bacitracin alone. In embodiments, the MBC of the combination is decreased by at least 2000-fold compared to the bacitracin alone. In embodiments, the MBC of the combination is decreased by at least 5000-fold compared to the bacitracin alone. In embodiments, the MBC of the combination is decreased by at least 10,000-fold compared to the bacitracin alone. In embodiments, the MBC of the combination is decreased by at least 100,000-fold compared to the bacitracin alone. In embodiments, the MBC of the combination is decreased by at least 200,000-fold compared to the bacitracin alone.

Certain gallate esters may be administered in the form of pharmaceutically acceptable salts which include the following non-limiting examples: alkali metal salts, such as those of lithium, potassium and sodium; alkali earth metal salts, such as those of barium, calcium and magnesium; transition metal salts, such as those of zinc; and other metal salts, such as those of aluminum, sodium hydrogen phosphate and disodium phosphate; salts of nitrates, borates, methanesulfonates, benzene sulfonates, toluenesulfonates, salts of mineral acids, such as those of hydrochlorides, hydrobromides, hydroiodides and sulfates; salts of organic acids, such as those of acetates, trifuoroacetates, maleates, oxalates, lactates, malates, tartrates, citrates, benzoates, salicylates, ascorbates, succinates, butyrates, valerates and fumarates. amine salts, such as those of N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris (hydroxymethyl)-aminomethane.

Pharmaceutically acceptable salts can be derived from inorganic or organic acids or can be derived from inorganic or organic bases as is known in the art. Basic amino acids useful for salt formation include arginine, lysine and ornithine. Acidic amino acids useful for salt formation include aspartic acid and glutamic acid.

Compounds of this disclosure and any salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, compounds herein may have trans and cis isomers and may contain one or more chiral centers, and therefore exist in enantiomeric and diastereomeric forms. The disclosure includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

With respect to the various compounds of the disclosure, the atoms therein may have various isotopic forms, e.g., isotopes of hydrogen include deuterium and tritium. All isotopic variants of compounds of the invention are included within the invention and particularly included at deuterium and $^{13}C$ isotopic variants. It will be appreciated that such isotopic variants may be useful for carrying out various chemical and biological analyses, investigations of reaction mechanisms and the like. Methods for making isotopic variants are known in the art.

All references throughout this application, for example patent documents including issued or granted patents or equivalents; patent application publications; and non-patent literature documents or other source material; are hereby incorporated by reference herein in their entireties, as though individually incorporated by reference.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

THE EXAMPLES

Example 1

Materials and Methods

Bacterial Strains and Culture Conditions.

MRSA (ATCC 33593), MSSA (ATCC 29213), and MRSA USA300 (BAA-1680) strains were purchased from the American Type Culture Collection (ATCC; Manassas, Va.). Eight clinical isolates of MRSA were obtained from the Culture Collection of Antimicrobial Resistant Microbes, Korea National Research Resource Center (KNRRC). *Salmonella enterica Typhimurium* LT2 was purchased from ATCC, and *Escherichia coli* O157:H7 is a kind gift from Dr. Sangryeol Ryu (Seoul National University, South Korea). All *S. aureus* strains were maintained in Trypticase Soy (TS) medium, and *E. coli* O157:H7 and *Salmonella* were routinely grown aerobically on Luria-Bertani (LB) media at 37° C. For measuring growth kinetics, an overnight culture of MRSA in Mueller-Hinton (MH) broth was diluted 100-fold in fresh MH broth and cultured until early exponential phase. The culture (200 µl) was transferred to each well of a sterile 96-well plate and incubated at 37° C. with bacitracin alone, alkyl gallate alone, and combination of bacitracin/alkyl gallates at various concentrations. The optical density at 600 nm ($OD_{600}$) was measured every hour with FLUOstar® Omega (BMG Labtech, Germany).

Reagents.

Bacitracin was obtained from Sigma-Aldrich (St. Louis, Mo.). A series of alkyl gallates, including gallic acid (GA), methyl gallate (MG), ethyl gallate (EG), propyl gallate[27], and lauryl gallate (LG), were purchased from Sigma-Aldrich. Butyl gallate (BG), octyl gallate (OG), and stearyl gallate (SG) were purchased from the Tokyo Chemical Industry (Tokyo, Japan). Sixteen other phenolic compounds were tested including butylated hydroxytoluene (BHT), tannic acid, sinapic acid, vanillic acid, cinnamic acid, caffeic acid, epigallocatechin gallate, chrysin, naringenin, hesperidin, quercetin, morin, taxifolin, salicylic acid, epicatechin, and catechin; all these compounds were purchased from Sigma-Aldrich.

Antibiotic Susceptibility Assay.

Broth micro dilution assays were performed to determine the minimum inhibitory concentrations (MIC) accordance to the M7-A7 protocol of the Clinical and Laboratory Standards Institute (CLSI) guidelines[28]. The susceptibility test was carried out with an initial bacterial inoculum of $1.5 \times 10^5$ CFU $ml^{-1}$. Alkyl gallates and bacitracin were serially diluted in a polystyrene 96 well plate and the plate was incubated at 37° C. for 24 h. Minimum bactericidal concentration (MBC) was determined by spotting 10 µl of cultures from MIC tests onto MH agar and incubated aerobically at 37° C.

Bacterial Membrane Permeability.

Membrane permeability was determined by measuring fluorescence after exposure of USA300 to propidium iodide as described previously[29]. Briefly, USA300 was grown in MH broth to the exponential phase and then diluted to OD600≈0.25. Propidium iodide was mixed with bacteria to a final concentration of 10 μM. Aliquots of 200 μL were then loaded into a black wall 96 microplate and agents were added at sub-MIC levels in triplicate. Fluorescence was monitored at excitation and emission wavelengths of 585 nm and 620 nm, respectively, for 1 h using FLUOstar Omega® (BMG Labtech, Germany). The membrane permeability was calculated by subtracting fluorescence intensity of controls without treatment with phenolic compounds from that of treated samples. EDTA (1 mM) was used as a positive control.

Biofilm Assay.

Biofilm assays were performed as described previously[30]. Briefly, overnight culture of MRSA was diluted 1:100 in TS broth and was grown in a 96-well microtiter plate in the presence or absence (a negative control) of combinations of bacitracin and lauryl gallate at different concentrations. After aerobic incubation at 37° C. for 18 h, biofilms were washed and stained with crystal violet. After washing unbound crystal violet, the absorbance at 630 nm was measured with FLUOstar Omega® (BMG Labtech).

Example 2

Determination of MIC and MBC in USA300

Prior to examining the synergistic effect between bacitracin and alkyl gallates, the MICs and MBCs of alkyl gallates were measured for MRSA USA300. Alkyl gallates exhibited antimicrobial activity against USA300 at high concentrations (Table 1).

Example 3

Growth Inhibition of USA300 by Bacitracin with Alkyl Gallates

Figures 1G, 1H:
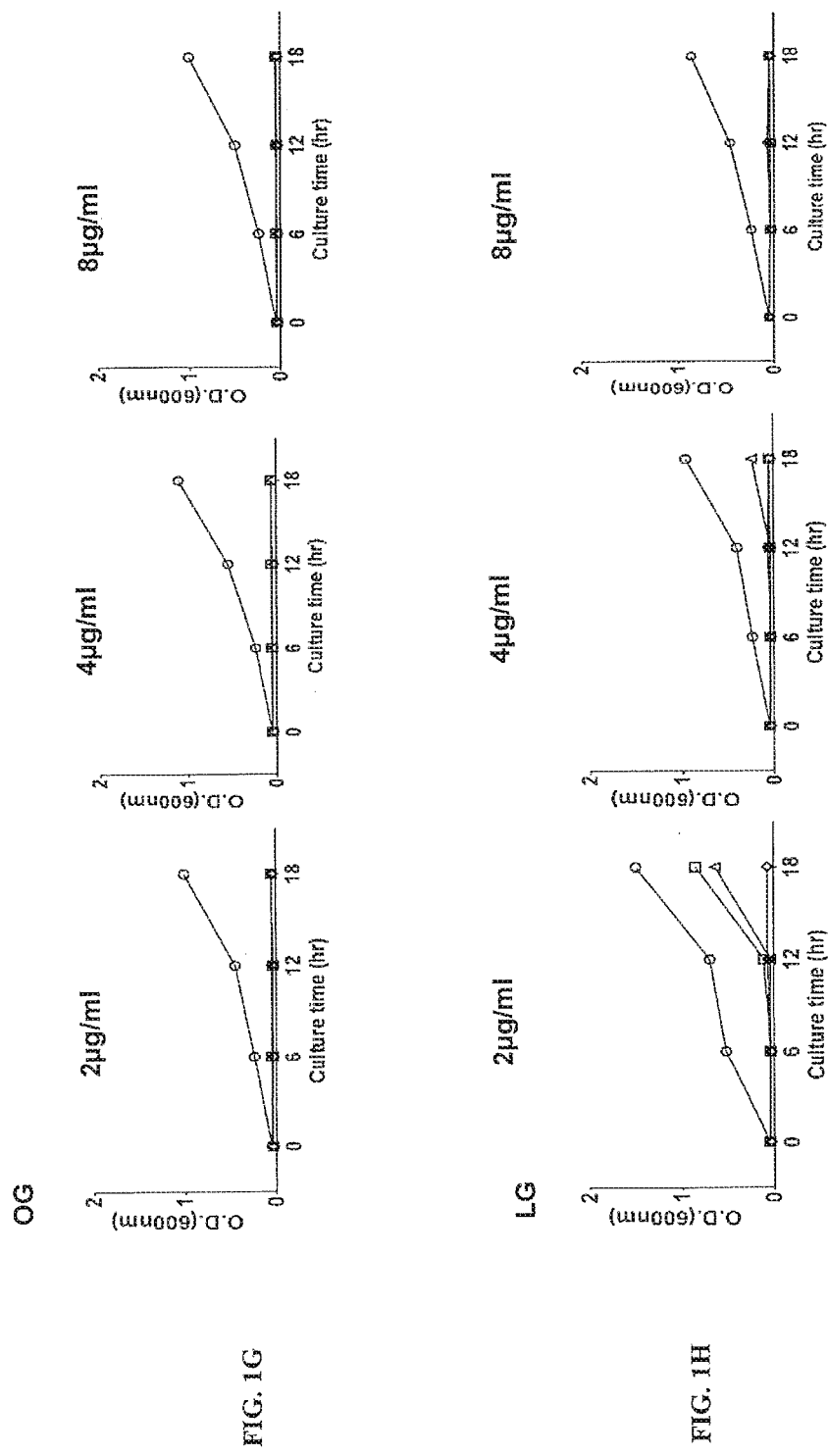
Figure 1I:
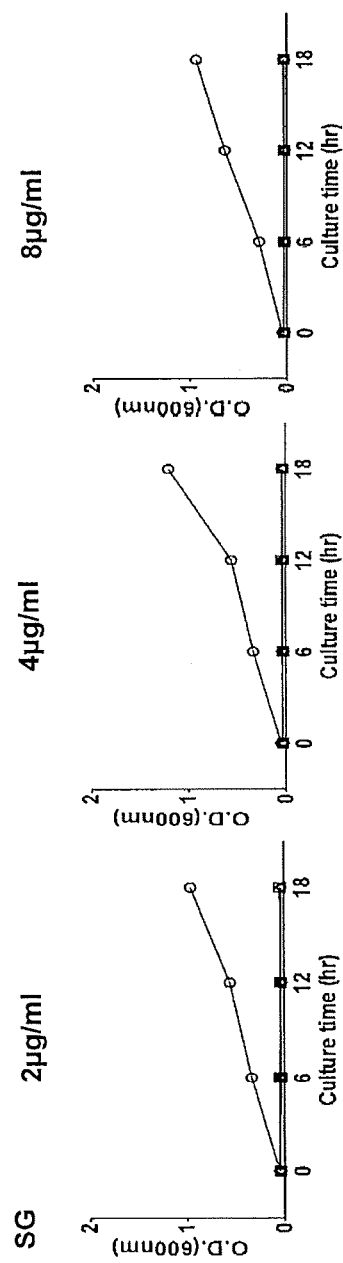

The growth curve of a control (USA300 treated with bacitracin only without alkyl gallates; FIG. 1A) showed that bacitracin did not inhibit USA300 even at the highest concentration used in the assay (i.e., 100 U). Bacitracin in combination with OG and stearyl gallate (SG) completely inhibited the growth of USA300 even at the lowest concentration (0.001 U) (FIGS. 1G, 1I). MG, EG, BG, and LG also exhibited significant growth inhibition against USA300 depending on the concentration (FIGS. 1C, 1D, 1F, 1H). The results successfully show significant synergistic anti-MRSA activity in combination of bacitracin with some alkyl gallates.

Example 4

Significant Bactericidal Activity of Bacitracin and Alkyl Gallates on USA300

Figure 2:
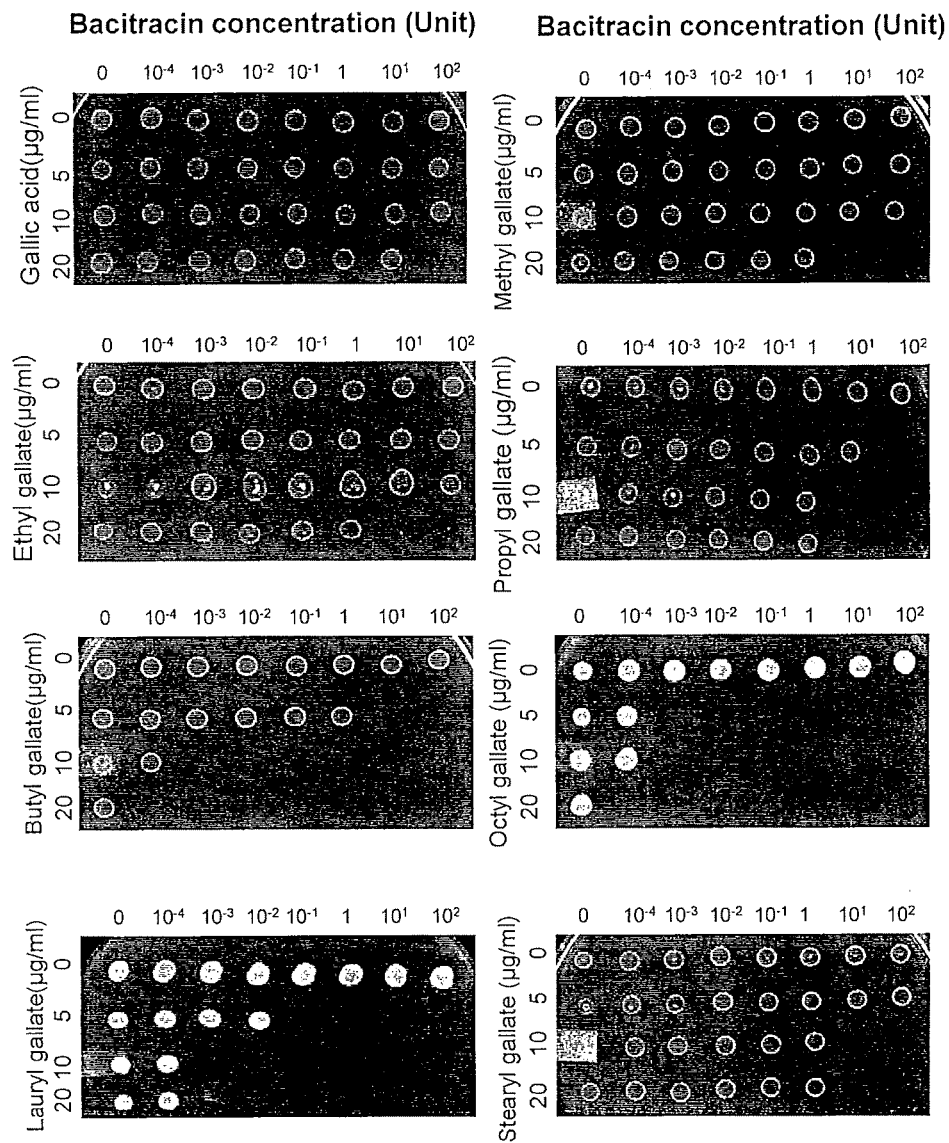
FIG. 2. Antimicrobial killing of USA300 by bacitracin and alkyl gallates. The concentrations of alkyl gallates are indicated on left, and bacitracin unit is marked on top. The experiment was repeated three times and produced similar results.

Since substantial growth inhibition of USA300 by bacitracin and alkyl gallates (see FIGS. 1A-1I) was observed, the bactericidal effect of the combinations on USA300 was determined. Most significant bactericidal activity was observed in combination of OG and bacitracin (FIG. 2). OG at 5 μg ml$^{-1}$ enabled 10$^{-3}$ U bacitracin to completely kill USA300 (FIG. 2), which is 200,000-fold decrease in MBC; bacitracin MBC is 200 U in USA300 (Table 1). With 20 mg ml$^{-1}$ OG, the MBC of bacitracin was further decreased to 10$^{-4}$ U (2,000,000-fold reduction in MBC) (FIG. 2). In addition, BG and LG supplementation also exhibited synergistic antimicrobial activity against USA300, but these compounds required relatively higher concentrations of alkyl gallates or bacitracin than OG. For example, the MBC of bacitracin was 10$^{-1}$ U with 5 μg ml$^{-1}$ LG (2,000-fold decrease in MBC). Although SG strongly inhibited the growth of USA300 (FIG. 1I), its killing effect was not as significant as OG, LG, and BG (FIG. 2), suggesting that the synergistic inhibitory effect of SG is bacteriostatic on USA300. In this experiment, it was found that OG, LG, and BG exhibited the most significant synergistic bactericidal activity against USA300 in combination with bacitracin.

Example 5

Figure 3:
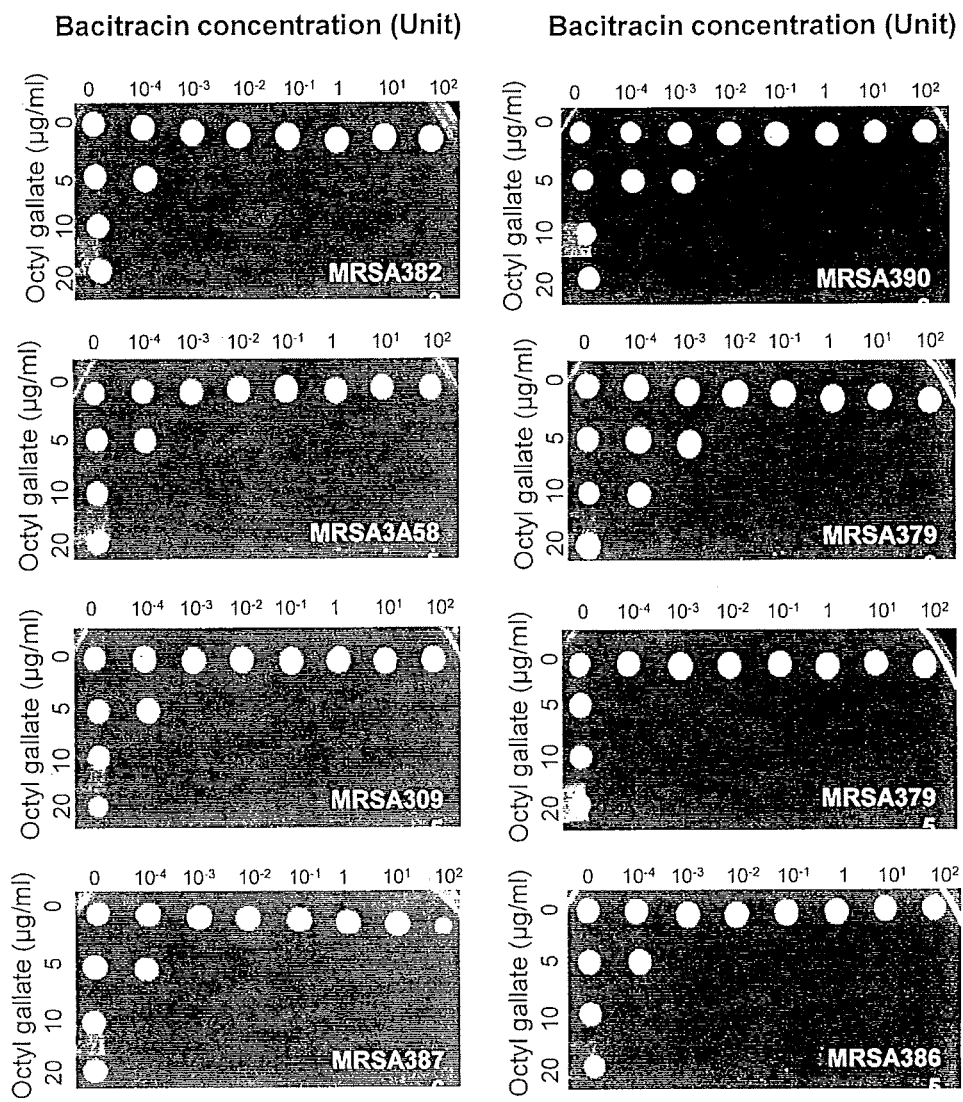
FIG. 3. Synergistic antimicrobial killing of clinical isolates of MRSA with hyper- and multidrug-resistance. Low concentrations of OG effectively killed clinical MRSA isolates with hyper-resistance.

Synergistic Bactericidal Activity of OG and Bacitracin Against Clinical Isolates To examine the synergistic anti-MRSA activity of OG and bacitracin, antimicrobial susceptibility tests were performed with human clinical isolates of MRSA with multidrug- and hyper-resistance. These clinical isolates were obtained from various sources, such as the nose, skin, and blood of human patients, and exhibited high level resistance to clinically-important antibiotics, such as oxacillin, erythromycin, chloramphenicol, gentamicin, and bacitracin as well (Table 2). Interestingly, OG plus bacitracin combinations successfully killed all the tested clinical MRSA isolates with hyper-resistance (FIG. 3). The MBC of bacitracin was 10$^{-2}$ U in MRSA 3903 and 3799 with 5 μg ml$^{-1}$ OG, whereas most strains were killed at 10$^{-3}$ U bacitracin at the same OG concentration (FIG. 3). These findings show that OG and bacitracin synergistically kill MRSA isolates with multidrug- and hyper-resistance.

Example 6

Changes in Membrane Permeability by OG

Figure 4A:
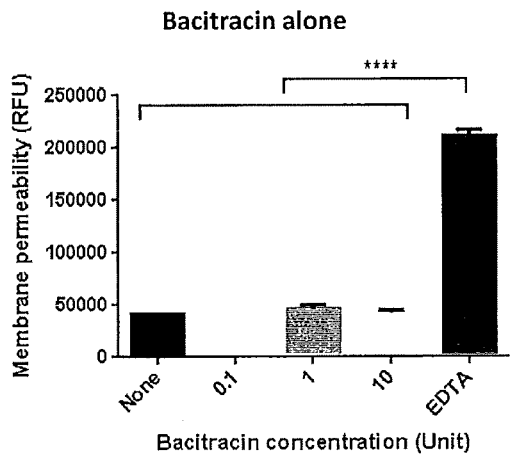
FIGS. 4A, 4B, 4C. Increased permeabilization of MRSA with OG and bacitracin. (A) Bacitracin treatment alone did not affect membrane permeability. EDTA (1 mM) was used as a positive control for permeability. (B) OG treatment increased the membrane permeability in MRSA. (C) Treatment with OG and bacitracin significantly altered membrane permeability. The statistical significance was determined by the Student's t-test. : P<0.05, *:P<0.01, ****:P<0.001.
Figure 4B:
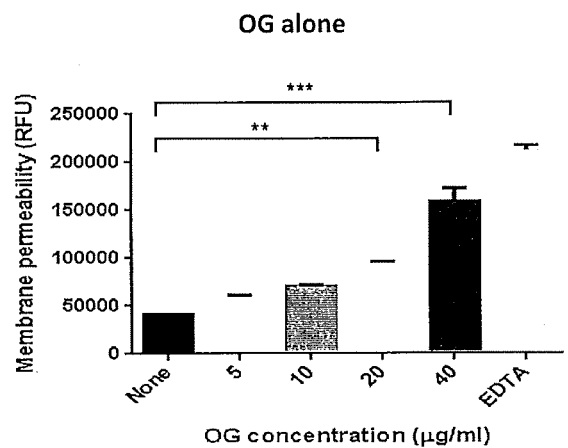
Figure 4C:
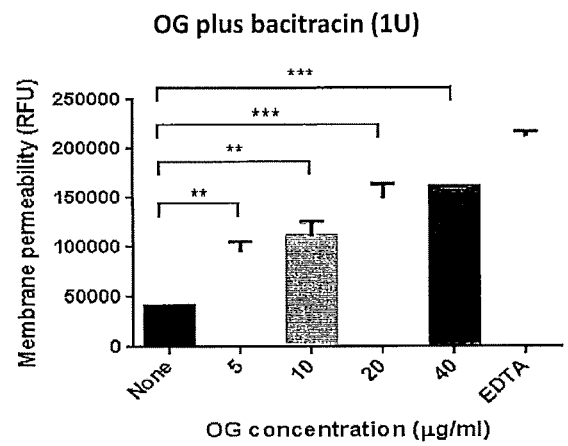

To explain how OG significantly enhances the anti-MRSA activity of bacitracin, changes in membrane permeability by OG were measured. Bacitracin itself did not affect membrane permeability, whereas 1 mM EDTA, a positive control, significantly increased membrane permeability (FIG. 4A). OG permeabilized the membrane in a concentration-dependent manner (FIG. 4B). OG in the presence of bacitracin more significantly increased membrane permeability than OG treatment without bacitracin (FIG. 4C). The results suggest that OG may enhance the antimicrobial activity of bacitracin by changing membrane permeability.

Example 7

Synergistic Anti-Biofilm Activity of Bacitracin and LG

Figure 5:
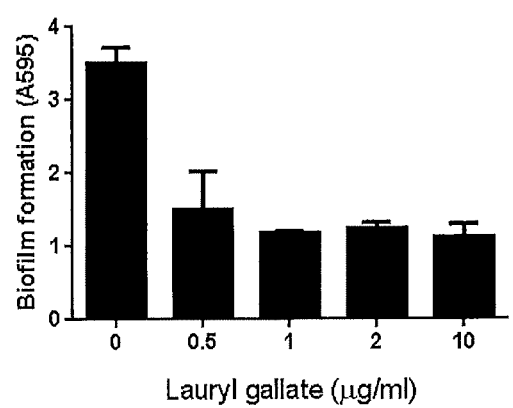
FIG. 5. Anti-biofilm activity of bacitracin and LG against MRSA USA300. In the assay, $10^{-4}$ U bacitracin was mixed with different concentrations of LG. The results show significant anti-biofilm effects of the bacitracin-alkyl gallate combination.

Since biofilm formation is an important process during infection, the effect of the bacitracin and alkyl gallate combination on biofilm formation was determined. LG plus 10$^{-4}$ U bacitracin exhibited a substantial reduction in the level of biofilm formation (FIG. 5). The results show that the bacitracin-alkyl gallate combination has an effective anti-biofilm activity.

Example 8

MIC Determination of Phenolic Antioxidants

MICs were determined with MRSA and methicillin-sensitive S. aureus (MSSA) using a broth dilution method as described above. Results are shown in Tables 3 (MRSA) and 4 (MSSA). Lauryl gallate, propyl gallate, tannic acid, and epigallocatechin gallate demonstrated relatively low MIC levels compared to other antioxidants in both MRSA and MSSA.

Example 9

Figure 6:
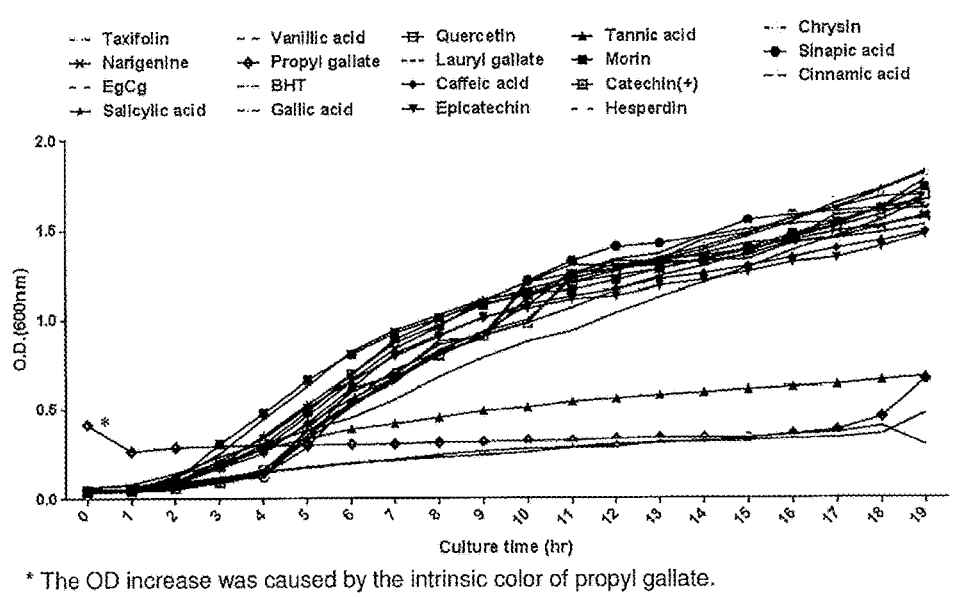
FIG. 6. Inhibition of MRSA growth by some phenolic antioxidants. Nineteen natural and synthetic phenolic compounds were screened to identify those that inhibit the growth of MRSA. MRSA was grown aerobically at 37° C.

Synergistic Inhibition of MRSA by Certain Antioxidants in Combination with Bacitractin MRSA were grown with bacitracin (0.002 µg/mL) with antioxidant (as shown) at 0.5 µg/mL. Results are shown in FIG. 6. Lauryl gallate, propyl gallate, tannic acid, and epigallocatechin gallate (EgCg) significantly inhibited the growth of MRSA at extremely low concentrations of bacitracin, even as low as 0.002 µg/mi. Compared to the bacitracin MIC for MRSA (2 µg/mL), antioxidants increased the susceptibility of MRSA to bacitracin by approximately 1000-fold. In contrast, BHT, the antioxidant that is currently used for Polysporin® ointment, did not show any synergistic effects with bacitracin.

Example 10

Synergistic Anti-MRSA Activity of Lauryl Gallate with Bacitracin

Figure 7A:
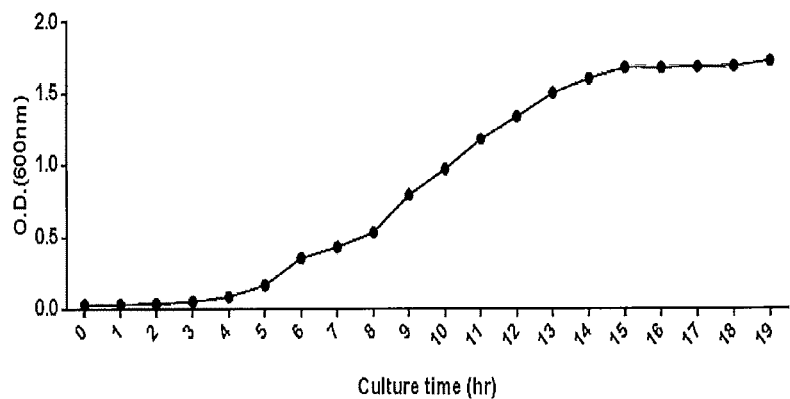
FIGS. 7A, 7B, 7C, 7D. MRSA growth without bacitracin (A), with different concentrations of bacitracin (B), with lauryl gallate (C), and 0.5 µg/ml lauryl gallate with different concentrations of bacitracin (10 µg≈1 U bacitracin) (D). The strain used in the experiment is a normal MRSA strain, NOT USA300.
Figure 7B:
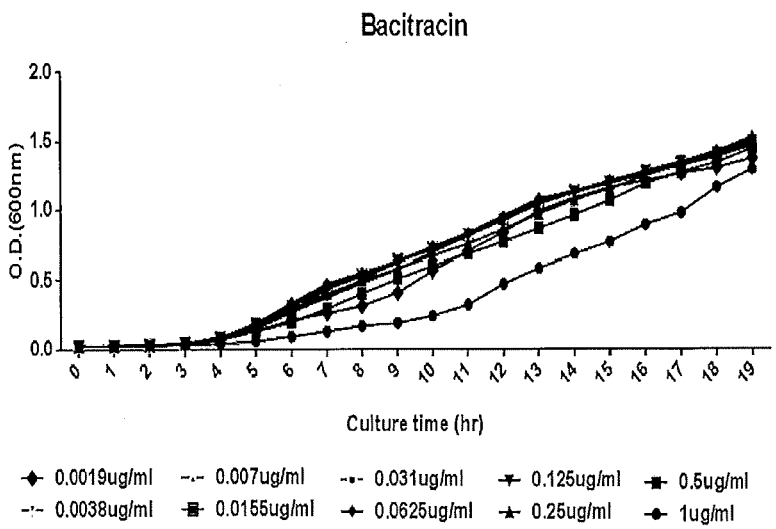
Figure 7C:
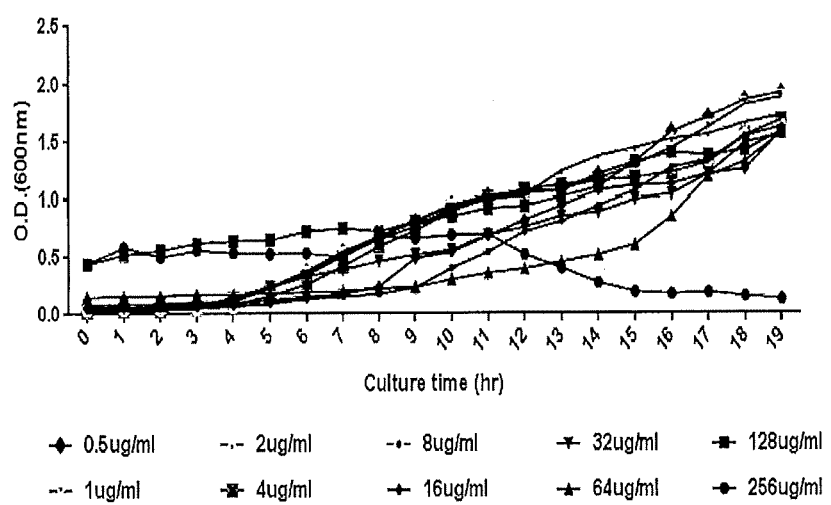
Figure 7D:
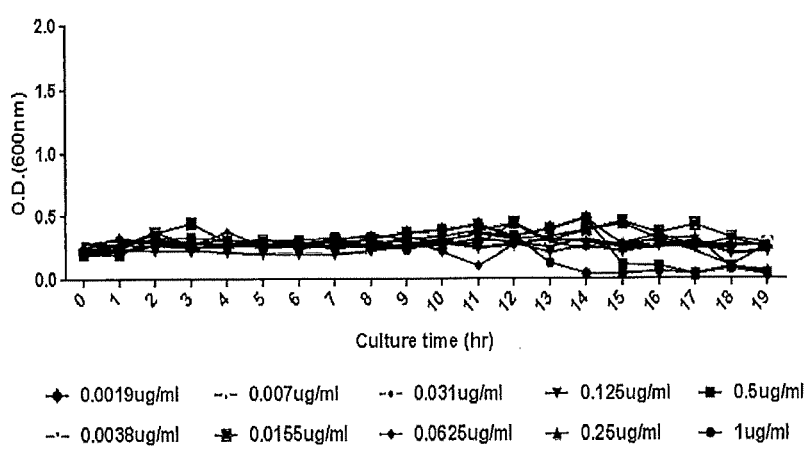
Figures 10A, 10B, 10C, 10D:
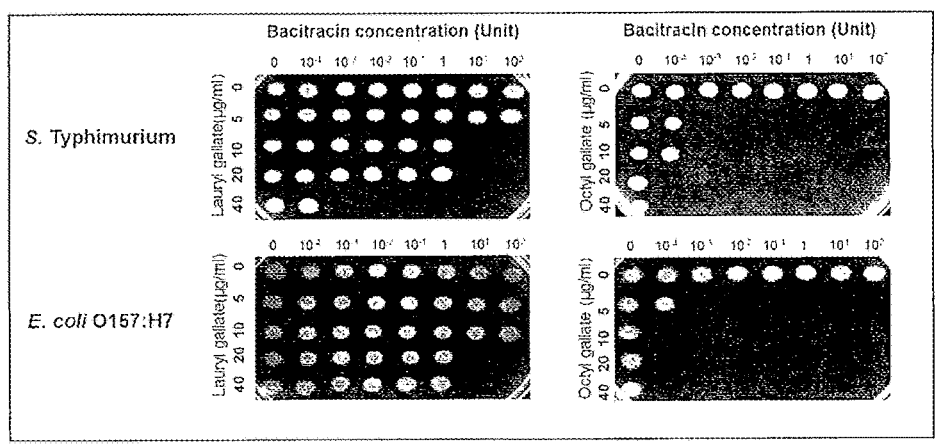
FIGS. 10A, 10B, 10C and 10D show synergistic bacitracin combinations made with lauryl gallate (LG) and octyl gallate (OG). Interestingly, OG exhibited a substantial (>1,000,000-fold in bacitracin MBC at 5 µg ml$^{-1}$ OG) antimicrobial activity against *Salmonella* and *E. coli* O157:H7, whereas LG showed more moderate synergistic effects.

Growth curves of MRSA are shown in FIGS. 7A, 7B, 7C and 7D. FIG. 7A is growth with no added bacitracin or lauryl gallate. FIG. 7B shows growth as a function of bacitracin concentration (0.0019 µg/mL to 1 µg/mL). FIG. 7C shows growth as a function of lauryl gallate concentration (0.5 µg/mL to 256 µg/mL). FIG. 7D shows growth in the presence of 0.5 µg/mL at varying concentrations of bacitracin (0.0019 µg/mL to 1 µg/mL). Bacitracin did not inhibit MRSA at concentrations used in this study (FIG. 7B). Lauryl gallate inhibited MRSA at the highest concentration (256 µg/ml) used in this study (FIG. 7C). Lauryl gallate (0.5 µg/ml) in combination with bacitracin synergistically inhibited MRSA growth. Similar growth inhibition patterns were observed in MSSA (data not shown).

Example 11

Synergistic Inhibition of MRSA Growth by Antioxidants

The optical density of MRSA was measured after 18 h culture with bacitracin (0.002 µg/ml) and antioxidants (as indicated at 0.5 µg/ml). Also measured were controls with no additions, with bacitracin alone and with antioxidant alone. FIGS. 8A, 8B, 8C and 8D are graphs illustrating the results. BHT showed no synergistic inhibition of growth in combination with bacitracin. The other antioxidants measured exhibited synergistic inhibition of growth in combination with bacitracin.

Example 12

Antioxidant Combination with Bacitracin Killed MRSA More Effectively than Bacitracin Alone MRSA and MSSA were cultured overnight with antioxidants (0.5 µg/ml) and bacitracin at various concentrations and 10 µL of the culture was spotted on MH agar plates and incubated aerobically at 37° C. to observe the bacterial viability. The results in FIGS. 9A, 9B, 9C and 9D (photographs of plates) show the Minimal Bactericidal Concentrations (MBCs) for indicated antioxidants. Bacitracin killed MRSA and MSSA at concentrations greater than or equal to 2 µg/mi. BHT did not generate any synergistic killing; BHT is a phenolic antioxidant used in Polysporin Compared to bacitracin alone, lauryl gallate more effectively killed MSSA (by >1,000-fold), and MRSA by 512-fold. Epigallocatechin gallate (EgCg) decreased the bacitracin MBC by 16-fold in MSSA and >32-fold in MRSA. Tannic acid decreased the MBC by 8-fold in MSSA and 4-fold in MRSA. Propyl gallate decreased the MBC by 16-fold in MSSA and 8-fold in MRS A.

Example 13

Synergistic Antimicrobial Activity of Bacitracin and Alkyl Gallates Against Gram-Negative Pathogens: *Salmonella enterica* Serovar. *Typhimurium* and *Escherichia coli* O157:H7

MIC and MBC were measured as described above. MIC and MBC data are shown in Table 5 for both the *Salmonella* and the *E. coli* strain tested. The tested strains were highly resistant to bacitracin.

FIGS. 10A, 10B, 10C and 10D show synergistic bacitracin combinations made with lauryl gallate (LG) and octyl gallate (OG). Interestingly, OG exhibited a substantial (>1,000,000-fold in bacitracin MBC at 5 µg ml$^{-1}$ OG) antimicrobial activity against *Salmonella* and *E. coli* O157: 117, whereas LG showed more moderate synergistic effects.

Combinations of bacitracin and octyl and lauryl gallate exhibited synergistic antimicrobial activity with Gram-negative *Salmonella* and *E. coli* strains.

REFERENCES

1 Stratton, C. W. *Clinical microbiology. [electronic resource]: quality in laboratory diagnosis*. (New York: Demos Medical Pub., c2012., 2012).
2 Montgomery, C. P., David, M. Z. & Daum, R. S. Host factors that contribute to recurrent staphylococcal skin infection. *Curr Opin Infect Dis* 28, 253-258, doi:10.1097/QC0.0000000000000156 (2015).
3 System, A. r. f. t. N. National Nosocomial Infections Surveillance (NNIS) System Report, data summary from January 1992 through June 2004, issued October 2004. *American journal of infection control* 32, 470-485, found at web page dx.doi.org/10.1016/j.ajic.2004.10.001 (2004).
4 Gould, I. M. Costs of hospital-acquired methicillin-resistant *Staphylococcus aureus* (MRSA) and its control. *International journal of antimicrobial agents* 28, 379-384, doi:10.1016/j.ijantimicag.2006.09.001 (2006).
5 Edwards, B. et al. Is vancomycin MIC "creep" method dependent? Analysis of methicillin-resistant *Staphylococcus aureus* susceptibility trends in blood isolates from North East Scotland from 2006 to 2010. *J Clin Microbiol* 50, 318-325, doi:10.1128/JCM.05520-11 (2012).
6 Boucher, H. W. et al. Bad bugs, no drugs: no ESKAPE! An update from the Infectious Diseases Society of America. *Clin Infect Dis* 48, 1-12, doi:10.1086/595011 (2009).

7 Otto, M. Basis of virulence in community-associated methicillin-resistant *Staphylococcus aureus*. *Annu Rev Microbiol* 64, 143-162, doi:10.1146/annurev.micro.112408.134309 (2010).

8 Gould, I. M. Community-acquired MRSA: can we control it? *Lancet* 368, 824-826, doi:10.1016/S0140-6736(06)69303-3 (2006).

9 Chambers, H. F. Community-associated MRSA—resistance and virulence converge. *The New England journal of medicine* 352, 1485-1487, doi:10.1056/NEJMe058023 (2005).

10 Fridkin, S. K. et al. Methicillin-resistant *Staphylococcus aureus* disease in three communities. *N Engl J Med* 352, 1436-1444, doi:10.1056/NEJMoa043252 (2005).

11 Lindenmayer, J. M., Schoenfeld, S., O'Grady, R. & Carney, J. K. Methicillin-resistant *Staphylococcus aureus* in a high school wrestling team and the surrounding community. *Arch Intern Med* 158, 895-899 (1998).

12 Groom, A. V. et al. Community-acquired methicillin-resistant *Staphylococcus aureus* in a rural American Indian community. *JAMA* 286, 1201-1205 (2001).

13 Zetola, N., Francis, J. S., Nuermberger, E. L. & Bishai, W. R. Community-acquired meticillin-resistant *Staphylococcus aureus*: an emerging threat. *The Lancet infectious diseases* 5, 275-286, doi:10.1016/S1473-3099(05)70112-2 (2005).

14 Moran, G. J. et al. Methicillin-resistant *S. aureus* infections among patients in the emergency department. *N Engl J Med* 355, 666-674, doi:10.1056/NEJMoa055356 (2006).

15 King, M. D. et al. Emergence of community-acquired methicillin-resistant *Staphylococcus aureus* USA 300 clone as the predominant cause of skin and soft-tissue infections. *Annals of internal medicine* 144, 309-317 (2006).

16 Adam, H. J. et al. Community-associated methicillin-resistant *Staphylococcus aureus*: prevalence in skin and soft tissue infections at emergency departments in the Greater Toronto Area and associated risk factors. *CJEM* 11, 439-446 (2009).

17 Gilbert, M. et al. Outbreak in Alberta of community-acquired (USA300) methicillin-resistant *Staphylococcus aureus* in people with a history of drug use, homelessness or incarceration. *CMAJ* 175, 149-154, doi:10.1503/cmaj.051565 (2006).

18 Bellman, B., Brandt, F. S., Hohmann, M. & Bebell, W. R. Infection with methicillin-resistant *Staphylococcus aureus* after carbon dioxide resurfacing of the face. Successful treatment with minocycline, rifampin, and mupirocin ointment. *Dermatol Surg* 24, 279-282 (1998).

19 Suzuki, M. et al. Antimicrobial ointments and methicillin-resistant *Staphylococcus aureus* USA300. *Emerging infectious diseases* 17, 1917-1920, doi:10.3201/eid1710.101365 (2011).

20 Wright, G. D. Resisting resistance: new chemical strategies for battling superbugs. *Chemistry & biology* 7, R127-132 (2000).

21 Pages, J. M. & Amaral, L. Mechanisms of drug efflux and strategies to combat them: challenging the efflux pump of Gram-negative bacteria. *Biochimica et biophysica acta* 1794, 826-833, doi:10.1016/j.bbapap.2008.12.011 (2009).

22 Hatano, T. et al. Effects of tannins and related polyphenols on methicillin-resistant *Staphylococcus aureus*. *Phytochemistry* 66, 2047-2055, doi:10.1016/j.phytochem.2005.01.013 (2005).

23 Shibata, H. et al. Triple combinations of lower and longer alkyl gallates and oxacillin improve antibiotic synergy against methicillin-resistant *Staphylococcus aureus*. *Antimicrob Agents Chemother* 53, 2218-2220, doi:10.1128/AAC.00829-08 (2009).

24 Shibata, H. et al. Alkyl gallates, intensifiers of beta-lactam susceptibility in methicillin-resistant *Staphylococcus aureus*. Antimicrobial agents and chemotherapy 49, 549-555, doi:10.1128/AAC.49.2.549-555.2005 (2005).

25 Kondo, K., Takaishi, Y., Shibata, H. & Higuti, T. ILSMRs (intensifier of beta-lactam-susceptibility in methicillin-resistant *Staphylococcus aureus*) from Tara [*Caesalpinia spinosa* (Molina) Kuntze]. *Phytomedicine* 13, 209-212, doi:10.1016/j.phymed.2004.08.001 (2006).

26 Administration, U. S. F. a. D. Food Additive Status List available at web site www.fda.gov/Food/IngredientsPackagingLabeling/FoodAdditivesIngredients/ucm091048.htm.

27 Sankar, B., Hopgood, P. & Bell, K. M. The role of MRSA screening in joint-replacement surgery. *International orthopaedics* 29, 160-163, doi:10.1007/s00264-005-0649-3 (2005).

28 CLSI. Methods for dilution antimicrobial susceptibility tests for bacteria that grow aerobically; approved standard M7-A7.CLSI, Wayne, Pa. (2007).

29 Nagant, C. et al. Identification of peptides derived from the human antimicrobial peptide LL-37 active against biofilms formed by *Pseudomonas aeruginosa* using a library of truncated fragments. *Antimicrob Agents Chemother* 56, 5698-5708, doi:10.1128/AAC.00918-12 (2012).

30 Darouiche, R. O., Mansouri, M. D., Gawande, P. V. & Madhyastha, S. Antimicrobial and antibiofilm efficacy of triclosan and DispersinB combination. *The Journal of antimicrobial chemotherapy* 64, 88-93, doi:10.1093/jac/dkp158 (2009).

31. Kubo, I., Xiao, P. & Fujita, K. Anti-MRSA activity of alkyl gallates. *Bioorg Med Chem Lett* 12, 113-116 (2002).

33 Kubo, I., Fujita, K., Nihei, K. & Masuoka, N. Non-antibiotic antibacterial activity of dodecyl gallate. *Bioorg Med Chem* 11, 573-580 (2003).

34 Pandey, K. B. & Rizvi, S. I. Plant polyphenols as dietary antioxidants in human health and disease. *Oxid Med Cell Longev* 2, 270-278 (2009).

35 Daglia, M. Polyphenols as antimicrobial agents. *Curr Opin Biotech* 23, 174-181 (2012).

36. See Broad Institute web site www.broadinstitute.org/annotation/genome/escherichia_antibiotic_resistance/MultiHome.html.

37. Wilkerson, C. et al. (2004) "Antibiotic Resistance and Distribution of Tetracycline Resistacne Genes in *Escherichia coli* O157:H7 Isolates from Human and Bovine," Antimicrob. Agents Chemotherapy, 48(3):1066-1067

38. Tadesse, D. A. et al. (2012) "Antimicrobial Drug Resistance in *Escherichia coli* from Humans and Food Animals United States 1950-2002," Emerging Infectious Diseases 18(5):741
39. D. Marzio, M. et al. (2013) "Antibiotic Resistance in *Samonella Typhimurian* Associates with CRISPR sequence type," Antimicrob. Gents Chemother. DOI: 10.1128/AAC.00913-13, Amer. SOc. *Microbiol.*
40. Rowe, B. et al. (1997) "Multi-drug Resistant *Salmonella typhi*: A Worldwide Epidemic," Clinical Infectious Disease 24 (Suppl. 1):S106-9 (University of Chicago).

TABLE 1

The MICs and MBCs of bacitracin, gallic acid, and alkyl gallates in USA300

| Strain | Agent | MIC/MBC (µg mL$^{-1}$) |
|---|---|---|
| USA300 | Gallic acid (GA) | 128/256 |
| | Methyl gallate (MG) | 128/256 |
| | Ethyl gallate (EG) | 128/256 |
| | Propyl gallate (PG) | 128/256 |
| | Butyl gallate (BG) | 512/1024 |
| | Octyl gallate (OG) | 32/64 |
| | Lauryl gallate (LG) | 32/64 |
| | Stearyl gallate (SG) | 1024/2048 |
| | Bacitracin | 1024/2048 (100U/200U) |

TABLE 2

Multidrug- and hyper-resistance patterns of human clinical MRSA isolates used in this study.

| MRSA | Origin | MIC (µg ml$^{-1}$) | | | | | | | | |
|---|---|---|---|---|---|---|---|---|---|---|
| | | BAC | OXA | PEN | ERY | CL | CIP | GEN | TET | NOR |
| 3799 | human/nose | 128 | ≥128 | 8 | ≥128 | ≥128 | 8 | 32 | 64 | 0.25 |
| 3876 | human/skin | 128 | 128 | 16 | ≥128 | <0.12 | 16 | 32 | 16 | 0.25 |
| 3865 | human/skin | 128 | 128 | 16 | ≥128 | ≥128 | 128 | 32 | 32 | ≥128 |
| 3095 | human/skin | 128 | ≥64 | | ≥128 | | | | | ≥128 |
| 3823 | human/nose | 64 | 128 | 16 | ≥128 | ≥128 | 8 | ≥128 | 64 | 32 |
| 3795 | human/nose | 8 | ≥128 | 16 | ≥128 | ≥128 | 32 | ≥128 | 16 | 0.5 |
| 3903 | human/skin | 32 | ≥128 | 32 | ≥128 | ≥128 | 16 | ≥128 | 128 | 64 |
| 3A585 | human/blood | 128 | >2 | | ≥4 | ≤0.25 | ≤1 | ≥8 | ≥8 | |

| MRSA | MIC (µg ml$^{-1}$) | | | | | | | |
|---|---|---|---|---|---|---|---|---|
| | GA | MG | EG | PG | BG | OG | LG | SG |
| 3799 | >1024 | >1024 | >1024 | 512 | 512 | 16 | 32 | >1024 |
| 3876 | >1024 | >1024 | >1024 | >1024 | 512 | 16 | 64 | >1024 |
| 3865 | >1024 | >1024 | >1024 | >1024 | 512 | 16 | 64 | >1024 |
| 3095 | >1024 | >1024 | >1024 | >1024 | 512 | 16 | 64 | >1024 |
| 3823 | >1024 | >1024 | >1024 | 512 | 512 | 16 | 64 | >1024 |
| 3795 | >1024 | >1024 | >1024 | 512 | 512 | 16 | 64 | >1024 |
| 3903 | >1024 | >1024 | >1024 | >1024 | 512 | 16 | 64 | >1024 |
| 3A585 | >1024 | >1024 | >1024 | >1024 | 512 | 16 | 64 | >1024 | where: BAC: bacitracin, OXA: oxacillin, PEN: penicillin, ERY: erythromycin, CL: chloramphenicol, CIP: ciprofloxacin, GEN: gentamicin, TET: tetracycline, NOR: norfloxacin, GA: gallic acid, MG: methyl gallate, EG; ethyl gallate, PG: propyl gallate, BG: butyl gallate, OG: octyl gallate, LG: lauryl gallate, SG: stearyl gallate.

TABLE 3

| MRSA | MIC(mg/L) | | |
|---|---|---|---|
| Gallic acid | >1024 | >1024 | >1024 |
| Butylated hydroxytoluene | >1024 | >1024 | >1024 |
| Lauryl gallate | 64 | 128 | 128 |
| Propyl gallate | 256 | 256 | 512 |
| Tannic acid | 512 | 1024 | 512 |
| Sinapic acid | >1024 | >1024 | >1024 |
| Vanillic acid | >1024 | >1024 | >1024 |
| Cinnamic acid | >1024 | >1024 | >1024 |
| Caffeic acid | >1024 | >1024 | >1024 |
| Epigallocatechin gallate | 512 | 256 | 512 |

TABLE 3-continued

| MRSA | MIC(mg/L) | | |
|---|---|---|---|
| Chrysin | >1024 | >1024 | >1024 |
| Narigenine | >1024 | >1024 | >1024 |
| Hesperedin | >1024 | >1024 | >1024 |
| Quercetin | >1024 | >1024 | >1024 |
| Morin | >1024 | >1024 | >1024 |
| Taxifolin | >1024 | >1024 | >1024 |
| Salicylic acid | >1024 | >1024 | >1024 |
| Epicatechin | >1024 | >1024 | >1024 |
| Catechin(+) | >1024 | >1024 | >1024 |

TABLE 4

| MSSA | MIC(mg/L) | | |
|---|---|---|---|
| Gallic acid | >1024 | >1024 | >1024 |
| Butylated hydroxytoluene | 1024 | >1024 | 1024 |
| Lauryl gallate | 64 | 64 | 128 |
| Propyl gallate | 128 | 64 | 128 |
| Tannic acid | 256 | 128 | 128 |
| Sinapic acid | >1024 | >1024 | >1024 |
| Vanillic acid | >1024 | >1024 | >1024 |
| Cinnamic acid | >1024 | >1024 | >1024 |
| Caffeic acid | >1024 | >1024 | >1024 |
| Epigallocatechin gallate | 128 | 64 | 128 |
| Chrysin | >1024 | >1024 | >1024 |

TABLE 4-continued

| MSSA | MIC(mg/L) | | |
|---|---|---|---|
| Narigenine | >1024 | >1024 | >1024 |
| Hesperedin | >1024 | >1024 | >1024 |
| Quercetin | >1024 | >1024 | >1024 |
| Morin | >1024 | >1024 | >1024 |
| Taxifolin | >1024 | >1024 | >1024 |
| Salicylic acid | >1024 | >1024 | >1024 |
| Epicatechin | >1024 | >1024 | >1024 |
| Catechin(+) | >1024 | >1024 | >1024 |

TABLE 5

| Compounds | E. coli O157:H7 | | S. Typhimurium | |
|---|---|---|---|---|
| | MIC(μg ml$^{-1}$) | MBC(μg ml$^{-1}$) | MIC(μg ml$^{-1}$) | MBC(μg ml$^{-1}$) |
| Bacitracin | >1024 | >1024 | >1024 | >1024 |
| Octyl gallate (OG) | 256 | 512 | 256 | 512 |
| Lauryl gallate (LG) | 512 | 1024 | >1024 | >1024 |

We claim:

1. A method for inhibiting the growth of Gram-negative and/or Gram-positive bacteria which comprises contacting the bacteria or an environment containing the bacteria with a combination of bacitracin and a gallate ester, wherein the gallate ester is octyl gallate, lauryl gallate or an aryl gallate ester.

2. The method of claim 1, wherein the gallate ester is octyl gallate or lauryl gallate.

3. The method of claim 1, wherein the gallate ester is an aryl gallate ester.

4. The method of claim 1, wherein the weight ratio of bacitracin to gallate ester is less than 0.1.

5. The method of claim 1, wherein the bacteria are Gram-positive bacteria.

6. The method of claim 1, wherein the bacteria are *Staphylococcus aureus*.

7. The method of claim 1, wherein the bacteria are methicillin-resistant *Staphylococcus aureus*.

8. A method for inhibiting the growth of Gram-negative bacteria which comprises contacting the bacteria or an environment containing the bacteria with a combination of bacitracin and a gallate ester.

9. The method of claim 8, wherein the bacteria are bacitracin-resistant Gram-negative bacteria.

10. The method of claim 8, wherein the Gram-negative bacteria are *E. coli* or *Salmonella* strains.

11. A method of treating a bacterial infection in an individual in need of such treatment which comprises administering to the individual a combined effective amount of bacitracin and a gallate ester, wherein the gallate ester is octyl gallate, lauryl gallate or an aryl gallate ester.

12. The method of claim 11, wherein the gallate ester is octyl gallate or lauryl gallate.

13. The method of claim 11, wherein the weight ratio of bacitracin to gallate ester ranges from 0.1 to 0.0001.

14. The method of claim 11, wherein the bacteria are Gram-positive bacteria.

15. The method of claim 11, wherein a wound is treated by applying the combination of bacitracin and the gallate ester to the wound.

16. The method of claim 11, wherein the gallate ester is an aryl gallate ester.

17. A method of treating a bacterial infection in an individual in need of such treatment which comprises administering to the individual a combined effective amount of bacitracin and a gallate ester, wherein the infection is a Gram-negative bacterial infection.

18. A pharmaceutical composition which comprises bacitracin and a gallate ester, wherein the gallate ester is octyl gallate, lauryl gallate or an aryl gallate ester.

19. The pharmaceutical composition of claim 18, wherein the gallate ester is octyl gallate or lauryl gallate.

20. The pharmaceutical composition of claim 18, wherein the gallate ester is an aryl gallate ester.

* * * * *